(12) United States Patent
Moore

(10) Patent No.: US 7,693,727 B2
(45) Date of Patent: Apr. 6, 2010

(54) EVIDENCE-BASED CHECKLIST FLOW AND TRACKING SYSTEM FOR PATIENT CARE BY MEDICAL PROVIDERS

(75) Inventor: Gordon T. Moore, Cambridge, MA (US)

(73) Assignee: Cerylion, Inc., Burlington, MA (US)

( * ) Notice: Subject to any disclaimer, the term of this patent is extended or adjusted under 35 U.S.C. 154(b) by 2090 days.

(21) Appl. No.: 10/440,465

(22) Filed: May 16, 2003

(65) Prior Publication Data

US 2004/0044546 A1 Mar. 4, 2004

Related U.S. Application Data

(60) Provisional application No. 60/381,191, filed on May 16, 2002.

(51) Int. Cl.
G06Q 50/00 (2006.01)
G06Q 40/00 (2006.01)
(52) U.S. Cl. .............................. 705/2; 705/4
(58) Field of Classification Search ...................... 705/2
See application file for complete search history.

(56) References Cited

U.S. PATENT DOCUMENTS 4,839,822 A 6/1989 Dormond et al.

(Continued)

FOREIGN PATENT DOCUMENTS

WO WO 00/41613 7/2000

OTHER PUBLICATIONS

Ginsberg, et al., "Staged Diabetes Management: Computerizing a Disease State Management Program", Journal of Medical Systems, Springer Netherlands: vol. 22, No. 2, 1998.*

(Continued)

*Primary Examiner*—Robert W Morgan
*Assistant Examiner*—Robert Sorey
(74) *Attorney, Agent, or Firm*—David A. Dagg

(57) ABSTRACT

Interactive methods and systems for directing, integrating, documenting, and tracking steps taken by medical providers during the process of care for a patient's given condition. Doctors' actions are directed by a prescriptive protocol—a checklist of discrete steps designed for efficient or optimal care of an individual patient's specific condition. The step-by-step checklist is abstracted from decision tree guidelines for the optimal work up and treatment for the condition using probability-based methodology. The care protocols can be derived from widely available and non-proprietary guidelines and decision trees based on public medical research literature.

In one embodiment, the invention can be employed by a primary care clinician at the point of referral into the specialist sector, and at the specialist level when proposing a risky or expensive or otherwise problematic medical or surgical diagnostic or treatment intervention. At these two critical transaction points in care, the checklist functions like a lock, based on a hidden clinical decision algorithm (an explanation of which can be displayed upon request). The system asks the clinician for data and then generates the patient's optimal checklist, displaying it as a point and click form keyed to the stage of care being undertaken by each doctor. As the clinician enters data into the checklist, a decision engine determines whether the checklist data satisfies predetermined criteria for authorization of the proposed action. The system can also document each transaction taken in the process of care to create an electronic record that can be made accessible to all clinicians involved in the process of care.

30 Claims, 23 Drawing Sheets

U.S. PATENT DOCUMENTS

| | | | |
|---|---|---|---|
| 5,517,405 A | 5/1996 | McAndrew et al. | |
| 5,574,828 A | 11/1996 | Hayward et al. | |
| 5,583,758 A | 12/1996 | McIlroy et al. | |
| 5,850,221 A | 12/1998 | Macrae et al. | |
| 5,953,704 A | 9/1999 | McIlroy et al. | |
| 6,049,794 A | 4/2000 | Jacobs et al. | |
| 6,056,690 A * | 5/2000 | Roberts | 600/300 |
| 6,188,988 B1 | 2/2001 | Barry et al. | |
| 6,256,613 B1 | 7/2001 | Falchuk et al. | |
| 6,353,817 B1 | 3/2002 | Jacobs et al. | |
| 7,020,578 B2 * | 3/2006 | Sorensen et al. | 702/181 |
| 7,076,437 B1 * | 7/2006 | Levy | 705/3 |
| 7,149,756 B1 * | 12/2006 | Schmitt et al. | 707/104.1 |
| 7,346,523 B1 * | 3/2008 | Provost et al. | 705/4 |
| 7,392,199 B2 * | 6/2008 | Karlov et al. | 705/2 |
| 2002/0019747 A1 * | 2/2002 | Ware et al. | 705/2 |
| 2002/0087361 A1 * | 7/2002 | Benigno et al. | 705/3 |
| 2002/0116221 A1 * | 8/2002 | Fields et al. | 705/2 |
| 2002/0188228 A1 * | 12/2002 | McNair et al. | 600/587 |
| 2003/0232314 A1 * | 12/2003 | Stout et al. | 434/322 |
| 2005/0020929 A1 * | 1/2005 | Murphy et al. | 600/509 |

OTHER PUBLICATIONS

INF 94-06 95-05719 00856327 NDN- 092-0085-8643-1, Schramm, Carl J., (abstract) "Technology: The real revolution", Insurance & Technology Health Insurance & Technology Supplement [online]. Retrieved from: INFORM: INF [retrieved on Feb. 25, 2002].

BNI 01-01-97 01699812 NDN- 173-0100-7224-8, Lawson, Cree, Mid-Tennessee Start-Up SYMED WEDS Health Care, High Tech for New Niche, The Nashville Banner [online]. Retrieved from: Database for Physician. [retrieved on Feb. 21, 2002].

* cited by examiner

Referral guideline tool

BUPA — the personal health service

Referral facilitator

Demographic data and referral reasons

| | |
|---|---|
| Menopausal status | Pre-menopausal ▾ |
| Bleeding with intercourse | ◯ Yes  ◉ No  ◯ Don't Know |
| Heavy bleeding | ◉ Yes  ◯ No  ◯ Don't Know |
| Pelvic Pain | ◯ Yes  ◉ No  ◯ Don't Know |
| Size of uterus in weeks | 10 |
| History of taking tamoxifen | ◯ Yes  ◉ No  ◯ Don't Know |
| History of polycystic ovaries | ◯ Yes  ◉ No  ◯ Don't Know |
| Prior genital tract cancer | ◉ Yes  ◯ No  ◯ Don't Know |
| Intermenstrual bleeding | ◯ Yes  ◉ No  ◯ Don't Know |

[ Submit data ]

FIG. 5

SPECIALIST STATUS REPORT

| REFRESH SCHEDULE | | FOR DAY | ◁ 2/13/2002 (WED) ▷ | | ◁◁ ▷▷ 1 ↕ 2 | |
|---|---|---|---|---|---|---|
| STATUS | PATIENT | MED REC # | LENGTH | LOCATION | | CHECKLIST GAP |
| ⊘ | VAZ, MANUEL J | 78261 | 30 | COMP: 7:49 AM | | No SGOT |
| ⊘ | BOOKER, JOYCE C | 496263 | 20 | COMP: 8:55 AM | | |
| ⊘ | BOYDEN, JOHN P | 2449677 | 30 | COMP: 8:50 AM | | |
| ⊘ | HEATHMAN, VIVIAN R | 194832 | 20 | COMP: 9:03 AM | | |
| ⊘ | ANDERSON, SAMUEL L | 144479 | 20 | COMP: 10:04 AM | | MRI, Rx |
| ⊘ | ELLIS, WALTER J | 44030 | 30 | COMP: 9:04 | | |
| ⊘ | ALACH, JAMES | 450824 | 20 | COMP: 10:11 AM | | Hct, BUN |
| ⊘ | ELBRUS, LYUBOV | 494554 | 20 | COMP: 10:07 AM | | Rx |
| ○ | LEFORT, AIDA C | 184312 | 30 | NO SHOW | | Rx |
| ⊘ | WAITERS, HATTIE B | 86856 | 20 | COMP: 11:08 AM | | 0 |
| ⊘ | RISMAN, BARBARA | 418235 | 30 | COMP: 1:24 PM | | |

FIG. 22

| ENCOUNTER HISTORY | | | | |
|---|---|---|---|---|
| DATE | TYPE | DEPARTMENT | PROVIDER | DESCRIPTION |
| 03/25/2002 | TELEPHONE | KENOBG | PARKER, DIANE RN | DYSFUNCTIONAL UTERINE BLEEDING |
| 03/21/2002 | TELEPHONE | KENOBG | PARKER, DIANE RN | DYSFUNCTIONAL UTERINE BLEEDING |
| 03/18/2002 | TELEPHONE | KENOBG | PARKER, DIANE RN | DYSFUNCTIONAL UTERINE BLEEDING |
| 03/04/2002 | TELEPHONE | KENOBG | DOWLING, DOROTH | NO SHOW |
| 03/04/2002 | APPOINTMENT | KENOBG | DOWLING, DOROTH | DYSFUNCTIONAL UTERINE BLEEDING |
| 03/01/2002 | TELEPHONE | KENOBG | PARKER, DIANE RN | DYSFUNCTIONAL UTERINE BLEEDING |
| 02/27/2002 | ORDERS ONLY | KENOBG | PARKER, DIANE RN | DYSFUNCTIONAL UTERINE BLEEDING |
| 02/27/2002 | TELEPHONE | KENOBG | PARKER, DIANE RN | DYSFUNCTIONAL UTERINE BLEEDING |
| 02/27/2002 | APPOINTMENT | KENOBG | PARKER, DIANE RN | NO SHOW |
| 02/25/2002 | TELEPHONE | KENOBG | LUCEY, ANNE RN | DYSFUNCTIONAL UTERINE BLEEDING |
| 02/19/2002 | TELEPHONE | KENOBG | PARKER, DIANE RN | TEST RESULTS ONLY |
| 02/19/2002 | TELEPHONE | KENOBG | PARKER, DIANE RN | DYSFUNCTIONAL UTERINE BLEEDING |
| 02/13/2002 | OFFICE VISIT | KENOBG | DOWLING, DOROTH | DYSFUNCTIONAL UTERINE BLEEDING |
| 02/13/2002 | OFFICE VISIT | KIM4E | MOORE, GORDON T | PREGNANCY EXAM / TEST |

CLICK ON TAB TO DISPLAY DETAILS

FIG. 23

EVIDENCE-BASED CHECKLIST FLOW AND TRACKING SYSTEM FOR PATIENT CARE BY MEDICAL PROVIDERS

RELATED APPLICATION(S)

This application claims the benefit of U.S. Provisional Application No. 60/381,191, filed May 16, 2002, the entire teachings of which are incorporated herein by reference.

BACKGROUND OF THE INVENTION

Medical care costs and quality are a serious problem facing America as well as other developed countries. Globally, costs are rising rapidly. About 80-90% of health care costs is for clinical services. It is widely documented, in reports such as Crossing the Quality Chasm (IOM, 2001), that these services, in virtually all countries, are inefficient, frequently unsafe, often not appropriate, and regularly not delivering services that have been shown to improve health. Estimates by experts suggest that upwards of 30% of the cost of clinical care is wasted on unnecessary and inefficient care.

This poor care is deeply imbedded in American health care delivery and financing methods. Many have said that our health care is a village industry and that industrial types of solutions might help better manage the transactions that constitute medical care.

There is a significant opportunity for improvement through rationalizing the process flow typical of medical care (we will call this the medical "supply chain")—with the patient usually moving from least to most technically complex care. These transactions for every patient with an episode of illness, and ultimately a single diagnosis, are currently unmanaged and poorly integrated and coordinated. The looseness of this process results in errors, omissions, missing information, duplication, re-work, inefficiency, sub-optimal quality, poor service, and high cost.

Many attempts have been made in the past to improve pieces or parts of the medical supply chain. These have ranged from utilization management—in which clinicians are asked to justify the appropriateness of their actions and to receive approval from the insurer—to putting large financial incentives in the hands of primary care doctors to manage care (so-called gate-keeping). While each of these appears to have some effect on reducing costs, concerns about quality, withholding of care, and double agent behavior of doctors have largely blocked these approaches. Utilization management, pre-authorization, and gate-keeping for pay have been waning and, as they have done so, medical costs have resumed an upward trajectory of 8-10% per year after five years of stability in the 1990's.

The use of expert guidelines is one approach that has been proposed to improve decision-making in health care. Expert guidelines are widely available commercially and publicly, and many sources exist for updating and publishing them to doctors in paper or electronic form. It has been claimed that new inventions in branching electronic decision support systems can guide and monitor the decisions that doctors make. Examples of such systems are discussed in, for instance, U.S. Pat. No. 5,953,704, to McElroy, et al., U.S. Pat. No. 6,049,794, to Jacobs, et al., U.S. Pat. No. 6,353,817, to Jacobs, et al, and U.S. Pat. No. 5,517,405, to McAndrew, et al.

Studies have shown, however, that such guidelines are rarely utilized by doctors and therefore have not had much impact on improving care. See, e.g., Effective Health Care: NHS Centre for Reviews and Dissemination. 5:1. February, 1999. ISSN:0965-0288; Davis D, Thomson M A, Oxman A D et al. Translating Guidelines into Practice. CMAJ. 1997; 157:408-16; Wensing M, Van der Weijden T R G. Implementing Guidelines And Innovations In General Practice. Br J Gen Pract 1998;48:991-7. In short, these guidelines have not been easily incorporated into the daily work of doctors so that they are feasible to use at the point of care and in the process of care. Most such systems provide so much information and are so complicated that doctors do not use them.

Other approaches to manage care have depended on electronic medical records (EMR), suggesting that these will provide the basis for documenting and structuring medical care. Electronic reminders and electronic prescription writing are good examples of an EMR approach to support good practice. However, electronic medical records have been resisted by most doctors and are in place in only four percent of medical practices in the U.S. These installations are largely in hospitals, and occasionally very large group practices. Therefore, few practices where decision tools are needed for support and integration of care actually employ a comprehensive EMR. Because of the high operating cost in time and money, many feel that comprehensive EMRs will be long in coming to office practice.

One of the primary problems with existing decision support tools is that they fail to adequately recognize and respond to how doctors actually do their work. Doctors are time constrained and practical. Any electronic support system should be easy to use in the workflow at the point of care and, so far, none of the present designs are. Moreover, an electronic support tool must deal with the true nature of the medical supply claim i.e.—that the process of care constitutes a series of linked handoffs, not independent acts taken separately by different doctors. Serious medical problems are managed as a series of integrated transitions and transactions, usually starting with a referral by a general practitioner or primary care clinician into the specialist and hospital sector. This train of events proceeds for an individual patient's episode of care for a condition, by a referral to a specialist based on the referring doctor's best diagnosis, then to increasingly specialized doctors for further opinions and study, and then often ends with a specialist delivering a complex diagnostic and treatment regimen, even surgery, to attempt to treat the problem. Each step is an input to the progression of care for what is usually a single problem and its ultimate resolution that "closes the case" on the episode. This constitutes the "supply chain" in medical care. Each step of the process is an input to the next. If done well, each step and handoff is appropriate and efficient, adds value, and contributes to the overall result. Done poorly, and the care suffers.

The time pressures of doctors and the disintegration of the work of doctors from one another makes designing a practical support system difficult. Typical guideline decision support tools are complicated and require considerable time to use. They often function more like textbooks than as a simple process support tool. Moreover, there is no system that supports, coordinates, and tracks the supply chain and links together care decisions, documentation, monitoring and feedback as the patient's care progresses.

SUMMARY OF THE INVENTION

The present invention relates to a system and method that enables health care providers, and primary care physicians in particular, to efficiently and effectively manage their patient's care into and throughout the specialist and hospital supply chain. In one aspect, the invention employs a simple checklist method of representing complex, expert based decision trees. This system simultaneously serves as an electronic checklist support system, a Web-based temporary electronic medical episode record, and a tracking tool that assists primary care physicians (and other doctors) to track patient progress. The invention is able to control process flow, facilitate communication and coordination between doctors, document medical care, and assure that all doctor "suppliers" using the system are operating to worldwide best standards of care. The system reduces the workload of doctors, minimizes the threat of malpractice, educates and improves the doctors who use it, and creates a mechanism for patients and doctors to share in the decisions about care.

According to one aspect, the invention comprises a condition-specific checklist accessed interactively via a computer network, such as the Internet. This checklist can be derived from publicly available guidelines or decision trees. While other currently utilized decision support systems present the actual decision engine and logic as flexible guidelines (i.e. a type of branching logic educational textbook for clinicians), the present system differs from the known decision support tools in that it first re-frames guidelines into a prescriptive format (variously called clinical care pathways, protocols, or criterion-referenced standards) based upon the patient's initial data and condition. This protocol, which is designed to be adhered to like a blueprint for medical care, is then translated into a checklist of data points, with the decision logic completely hidden from the user behind this simple checklist representation. The underlying logic and even advice and references can be made available if desired, but the interface with the doctors is normally kept uncomplicated.

In one embodiment, this simple checklist is further refined into a type of PERT, or flow chart, reflecting data points on an optimal cost-effective pathway for care. Two data inputs can be used to optimize the path in real time. First, the system tailors the generic checklist to the specific condition of each patient by applying probability theory (Sox, Probability Theory in the Use of Diagnostic Tests. Annals of Internal Medicine, 104:60-66, 1986.) The optimal protocol for each patient depends on the cost, risks, and added value of every test or maneuver performed in the work up. With the proper patient data about the prior likelihood of the suspect condition (entered by the Primary Care Clinician), Bayes' theorem can be applied automatically to calculate the value of any and every test or maneuver (i.e. an item of medical history or a physical examination finding) using the test or maneuver's sensitivity and specificity,—the two universal descriptive characteristics of test performance. The system can assist the primary care doctor to estimate the patient's prior probability of the illness. The system can then use this information to calculate the value of variations in the protocol, yielding a unique, patient-specific checklist that represents the optimally effective pathway or sequence for the patient.

A second input is that, as each successive data point is entered into the checklist, an underlying logic can be applied to calculate and change the conditional probabilities, and thus dynamically modify the checklist in real-time to optimize the number, sequence, and type of responses (tests and maneuvers) needed.

While assisting through all the transactions represented on the checklist, the invention generally acts most powerfully at, and tightly integrates, the transactions at two critical transition points of care that dominate the performance of the supply chain.

These are the handoff of the patient from the primary doctor to the specialist and the point at which a specialist undertakes complex, expensive, and risky testing or treatment, especially surgery. Underlying these two steps are clusters of data points, linked to decision algorithms, that function like a lock on a gate. The checklist data are the key to opening the gate. Once the gate (referral to the specialist, ordering an expensive new drug, or approval for the test, procedure or surgery) is "unlocked" by the proper data, the patient's care is automatically approved and appropriate payment can be authorized.

The system creates an especially "tamper-proof" lock at the specialist level. Since the care pathway always starts with the primary care clinician's data, the present system can use these prior data to create a two-key (like a safety deposit box) lock at the specialist level. Data elements entered by the primary care clinician are automatically re-entered on the checklist and become part of the lock and key at the time the specialist proposes care that must be approved. By having data that must be agreed by at least two different doctors, the quality and reliability are enhanced and the likelihood is lowered significantly that data could be manipulated by a specialist to win approval for proposed care.

The present invention can function in an interactive electronic environment. Both software and the temporary medical record structure can be made available as an Application Service Provider capable of operating as a standalone or dropped into an insurer's IS environment and behind its privacy firewall. Doctors can gain access to the tools and the patient record via the Web, preferably using a security device. Data are input by the patient's doctors selecting from point and click representations. Both input to and display of the record can be on any interface device that accesses the web (computer, handheld device, wap phone, voice recognition system, etc.).

The present system can also document steps of medical care as a standalone temporary episode record, which participating doctors can access and use anywhere and at anytime. While providing all the functionality of an EMR (one record, used by all clinicians to integrate care, document their specific actions, and communicate the results and status) to support their care for the specific episode, the "mini"-record of the present system does not require that the doctors use, pay for, or implement an EMR.

Like a PERT chart assists a builder, the final checklist guides the actions of the doctor and also can alert them if the actions are not followed. As the primary care doctor and then each subsequent specialist points-and-clicks his or her way through the checklist, hidden inference engines and decision rules logic can test whether or not the sequence and the data at each step meet the built in decision criteria. If they do, the collected data are incorporated and passed on to the next stage in the supply chain. At each stage in the supply chain additional clinical data points are requested and added to the patient's unique episode record. If the checklist data do not satisfy the decision criteria, the system can warn the doctor responsible for care at that point and, on request, provide documentation of the gap, supply literature or expert advice about the problem.

Since data are recorded as a temporary episode record, this electronic record can transmit, monitor, record, and provide instant access to all process information. It assures faultless and timely communication between all those involved in an individual patient's care.

In one aspect, the present system tracks and ties together the progress of care and provides primary care doctors with information that enables them to monitor and manage the patient's care. The temporary episode record integrates all transactions entered through the system. Algorithms can automatically extract tracking data that describes both logistic (where, what, and when) and quality performance (appropriate, comprehensive, safe) of the patient's care. These can be published back to the primary care doctor as part of a progress report on all patients undergoing active care by specialists. These measures are preferably displayed in an easy-to-read screen. Armed with continuously updated information presented in a simple scorecard, primary care doctors (and patients) are enabled to coordinate and optimize the process sequence of care of individual patients. With this report, which can highlight and warn the primary care doctor when there are problems with one of his or her patients (delays or decisions that are off the expert pathway), primary care doctors will be enabled to manage their patient's care electronically and easily. At the same time, if the specialist "data key" fails to unlock the approval gate, the system can notify the primary care doctor and, if the specialist chooses to appeal the algorithmic decision, the primary care doctor will be the first to adjudge the need.

When the episode is completed (specialist's care is finished and the patient is returned to primary care), the temporary episode record can be copied, either electronically or in paper form, and can be amalgamated with the patient's overall medical record. The temporary episode record can also be stripped of its patient identifiers, put in a system-wide data base, and expunged from the active system data base. This system-wide database can aggregate data across all patients, doctors, and insurers using the system. It supports analysis of medical care by condition, insurer, doctor, and other parameters, and it can create epidemiological information that can be used to understand care, compare it to that delivered by others, and support management to improve operational and clinical processes. In one aspect, data from this system-wide database can be used to help estimate the prior probability that a particular patient has a suspect condition, thus further optimizing the specific checklist or treatment protocol for the patient's care.

The present invention takes a unique approach to improving the flow of patients into, and throughout, the health care supply chain. The methods and systems of the invention need not rely on branching, interactive guidelines, but instead can utilize simple checklists that are derived from, and are simple representations of, underlying guideline logic. Also, unlike other lists (such as the lists promulgated by Physician Standard Review Organizations (PSRO) in the 1960's and 70's), the checklists of the present invention can be brought interactively to the point of care via modern electronic communication media, and they can simultaneously serve as a trackable, patient-specific medical record of the episode of care. Also, the checklists of the present invention are generally research evidence based, modifiable and customized based on individual patient data, continuously updated with new information and research, and accessible at the point of care in real time. In this way, the present invention provides a very simple tool for primary care clinicians to assure that their performance, and that of every subsequent doctor providing care in an episode of illness, achieves expert standards of quality.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 5 and 6 depict the criterion-referenced checklist gating a typical referral;

FIG. 22 depicts the primary care specialist tracking summary screen; and

FIG. 23 depicts the patient tracking detail screen.

DETAILED DESCRIPTION OF THE INVENTION

A description of preferred embodiments of the invention follows.

The present invention provides an evidence-based checklist of criteria for referral or procedures to primary care and specialist clinicians to assure that standards in these processes are met. By entering prompted patient information, the clinicians call up a customized optimal checklist that reminds, guides, and approves the clinician's actions.

Figure 1:
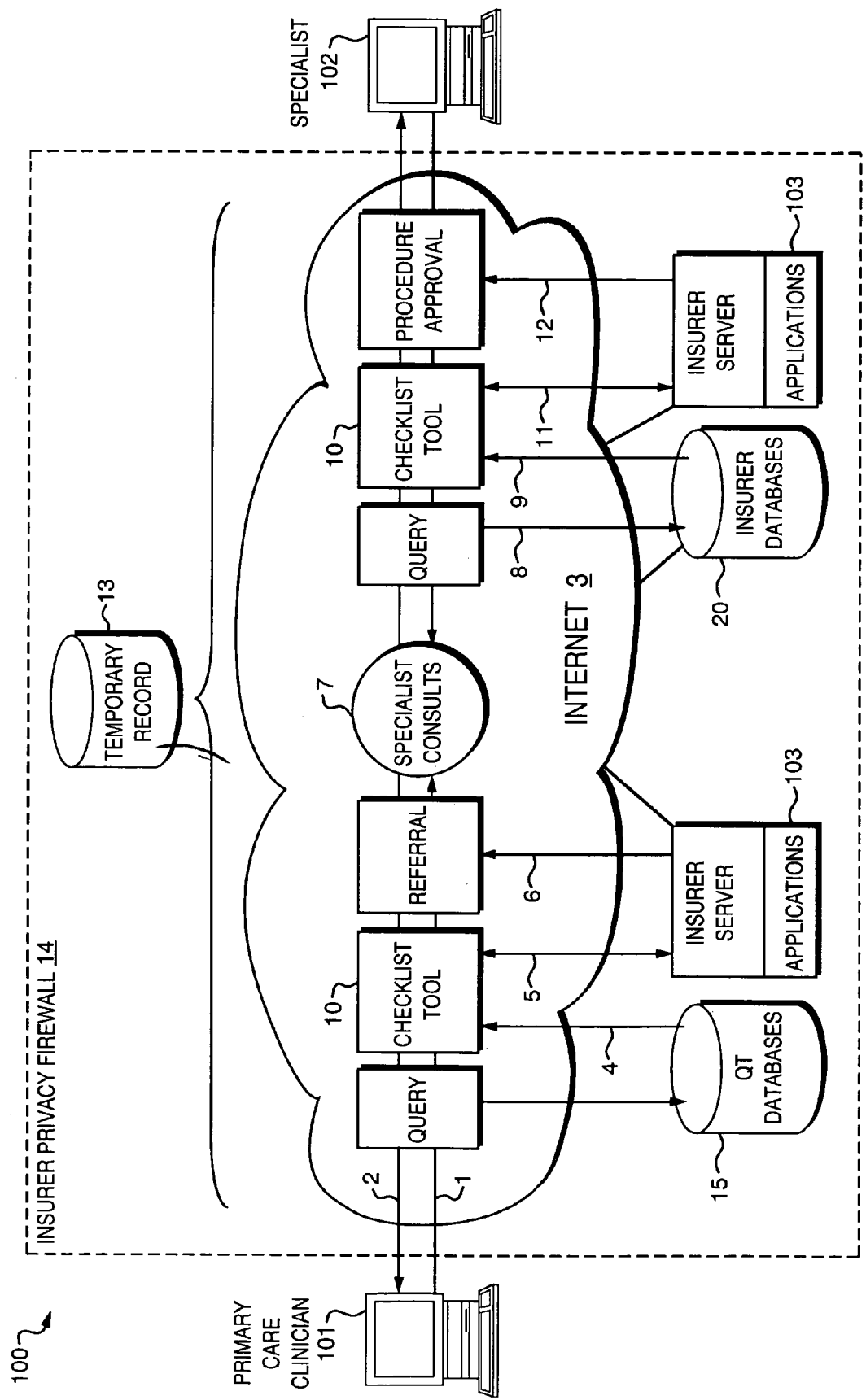
FIG. 1 is a schematic diagram of the hardware and general interactive environment in which the invention operates.

A general block diagram of one embodiment of the system is provided in FIG. 1. A primary care clinician interfaces with the system 100 via a user interface, which can comprise a desktop, handheld device, a WAP phone, or all other devices that access the Internet. The user is connected, through any communication path through the Web 3, to at least one database maintained behind an insurer's privacy firewall 14. The at least one database can include one or more system databases 15 (such as a guideline/checklist database, a prior probability database, a procedure threshold approval database, and a temporary episode record database), and one or more insurer databases 20 (such as a consultant database, a primary care doctor database, an eligibility database, a laboratory, an X-ray vendor, and a claims payable database).

Via guided questions keyed to the type of referral 2 being proposed, the clinician enters data 1, which are operated upon by a decision engine 5 (located in server 103) utilizing probability-theory (e.g. Bayesian) logic, to generate a specific and unique check list 10 of actions that are the required inputs to an appropriate referral. Further queries for items of data may be directed to the primary clinician based on logic imbedded in hidden, condition-specific decision trees. Once criteria for referral have been satisfied, the gate for the referral is opened and a referral note 6 is generated from the data entered and from information in the insurer's database.

The specialist clinician interfaces with system 100 via any user interface 102 and receives the information from the primary clinician, accessing it from a confidential and secure temporary, electronic recording 13 of prior transactions in the clinical episode. Upon completion of the consultation 7 with the patient, the specialist can enter data, in structured or free form, for electronic transmission back to the referring primary clinician. Alternatively, the specialist clinician may propose to order further tests or plan a procedure 8. These proposed actions generate guided questions 9 from the database, to which the clinician responds. From these data, a Bayesian decision engine generates a specific and unique check list of actions 10 that represent the required inputs 11 for the requested next step, which is determined by the insurer's server using predetermined decision criteria. Once criteria have been satisfied, the gate for the proposed action is opened and approval authorization 12 is delivered. All these transactions and sequencing are monitored, recorded in the temporary recording, and published back to the primary clinician in a standardized format that allows the primary clinician to track the care of individual patients.

Figure 2:
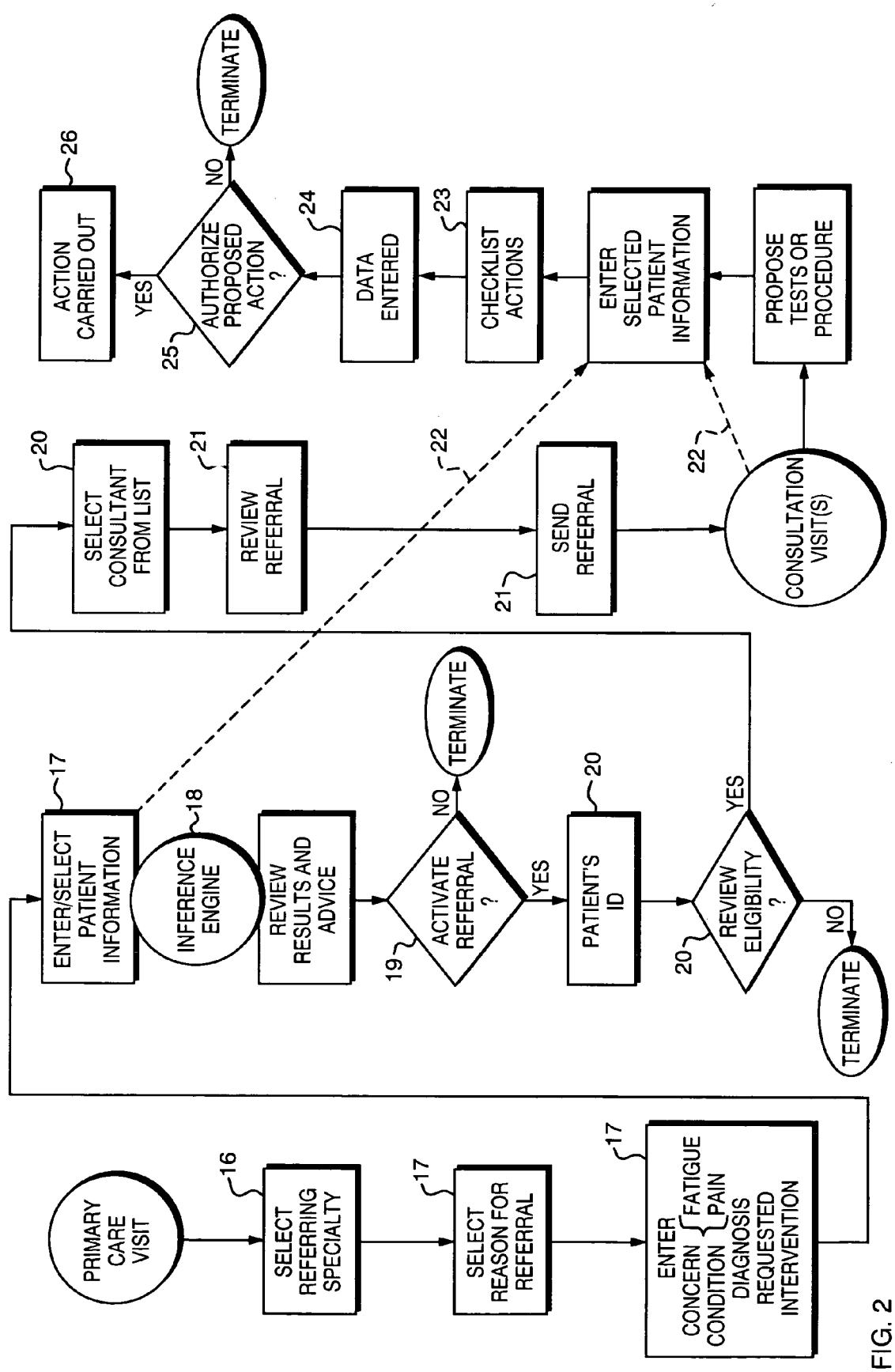
FIG. 2 is a high level flow diagram of the system.

FIG. 2 depicts a high-level flow diagram of the authorizing process. The referring primary care clinician selects the referral specialty 16 (and optionally, but not necessarily, a particular specialist physician) and enters descriptive patient information 17. Inference engine 18 operates on this data using Bayes' formula to produce a patient-specific interactive checklist of actions and data required for authorization of the specialist referral. Easily-understandable medical representations of the checklist items are then presented to the primary care physician, in sequence or in list form, and the referring physician enters requested data for each checklist item. As each item of data is entered into the checklist, the inference engine 18 uses decision logic to determine whether or not the data satisfies the pre-determined criteria for authorization of the referral. The inference engine 18 can also use the data entered into the checklist to update the remaining checklist items, modifying the number and sequence of remaining checklist items to further optimize the list to the patient's particular medical condition. The inference engine can also provide feedback and advice to the primary clinician regarding the patient's care. At step 19, the inference engine 18 notifies the primary care physician whether or not the criteria for referral have been satisfied. At this stage, the primary physician may choose to discontinue the referral and terminate the session. If the requested referral is authorized, however, the physician can then activate an automated referral process. It should be noted that in some embodiments, the primary physician may be permitted to override a refusal in certain circumstances, and proceed with the proposed referral.

If the physician proceeds with the referral, the patient's identifying information is entered 20 and eligible specialist consultants are pulled from the insurer's data base 20 and published to the referring primary clinician. If the particular specialist for referral has not already been identified, the referring physician then selects a specialist from the list. The system can automatically generate the referral note, which is reviewed and optionally modified by the primary care physician, and then automatically transmitted to the specialist at step 21.

The specialist then sees the patient and either completes the consultation or requests further tests or a procedure. If the specialist determines that a costly or potentially risky course of treatment or testing is needed, the specialist logs onto the system 100 and selects the proposed treatment or test from a list of possible medical actions. Patient information from the primary clinician and the specialist automatically populates the action checklist 22, and a new checklist 23 of remaining required information for authorization of the proposed action is generated by an inference engine. Once all required criteria on the check list have been satisfactorily entered 24, automatic authorization 25, or the action steps, is given to the specialist and the proposed action is carried out. 26.

Figure 3:
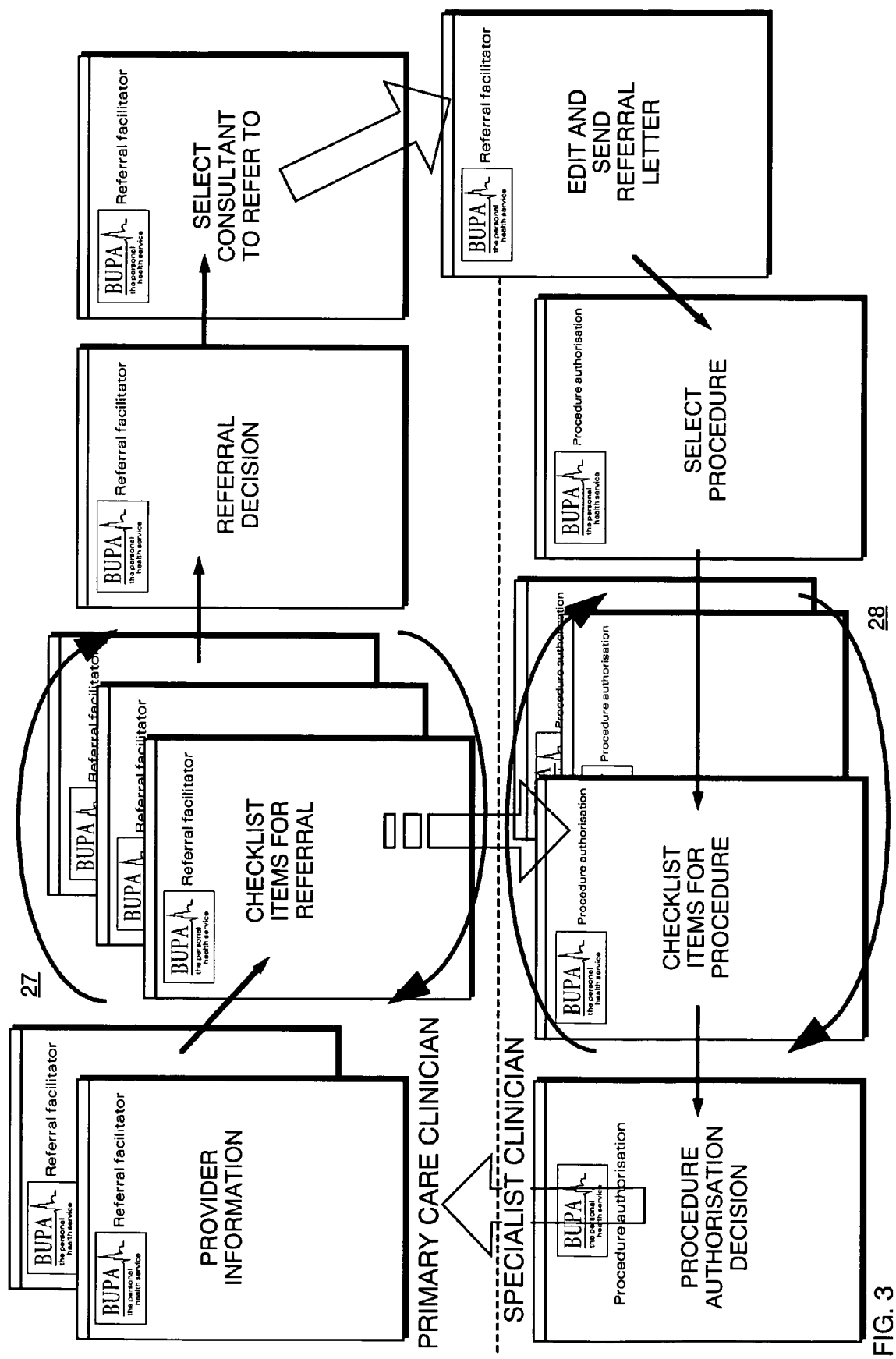
FIG. 3 is a pictorial representation of the system.

FIG. 3 is a pictorial representation of the system. Sequential steps are shown with 27 and 28 representing the inference engine operating on the check list to determine if minimal criteria have been met so that the referral 27 and the request for further tests or procedure 28 are appropriate and authorized according to expert, evidence-based criteria. The criteria can be determined by an insurance provider, for instance, or physicians' group leaders.

Figure 4:
FIG. 4 depicts the referring primary care clinician screen.
Figure 6:
Figure 7:
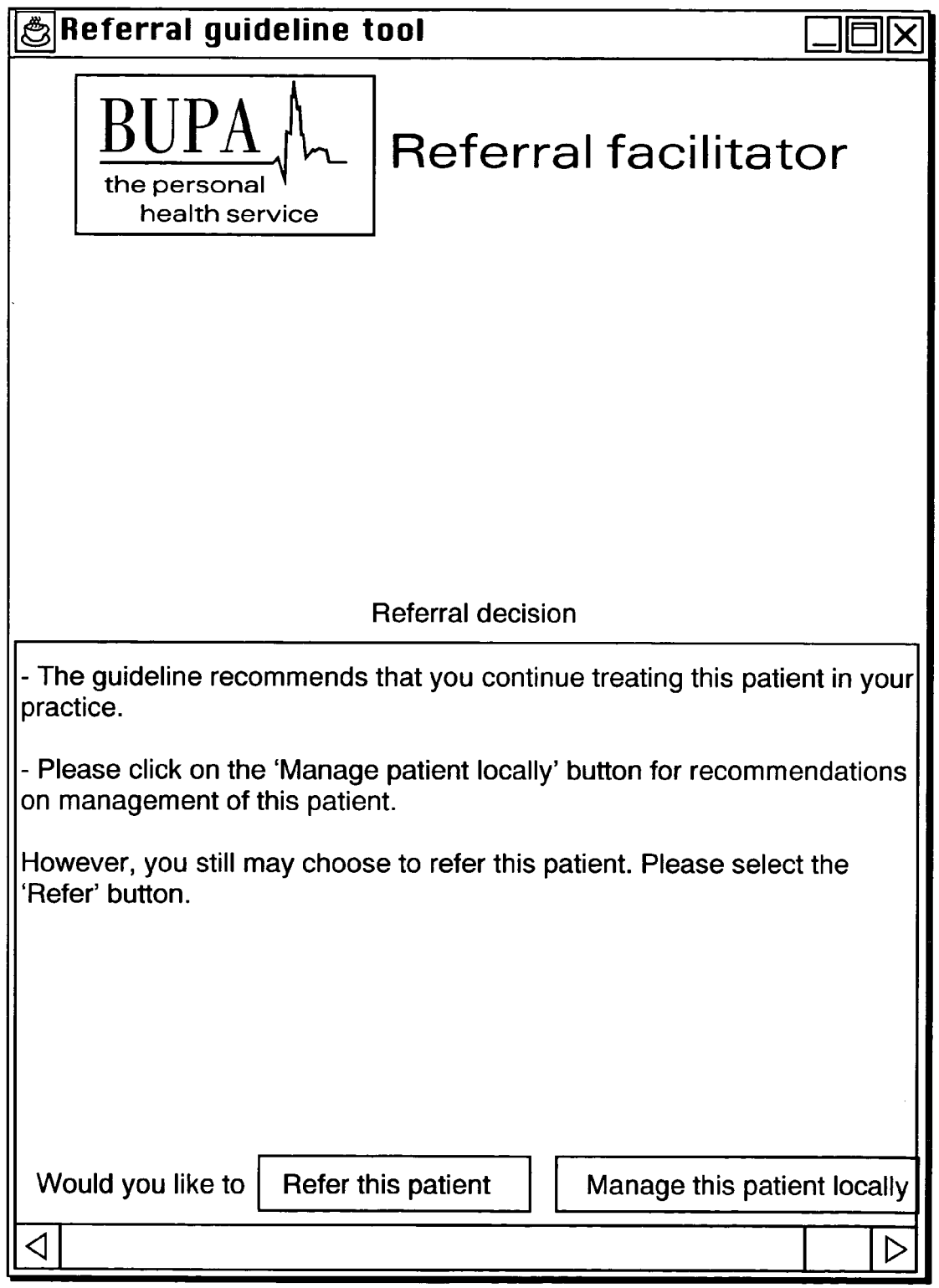
FIG. 7 shows the primary care clinician screen of approval or other actions needed.
Figure 8:
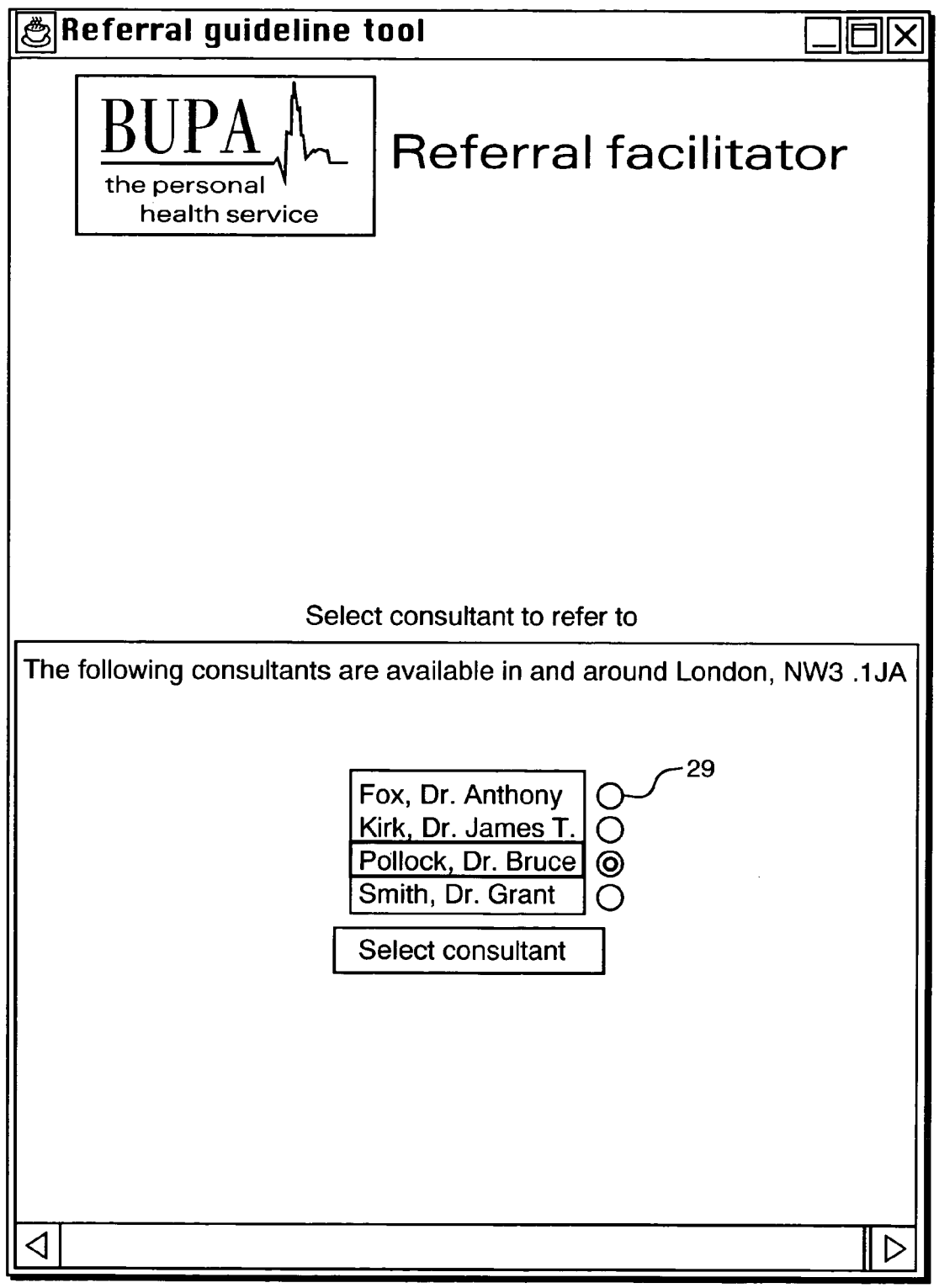
FIG. 8 depicts the primary care clinician's screen of participating specialists eligible for referral.
Figure 9:
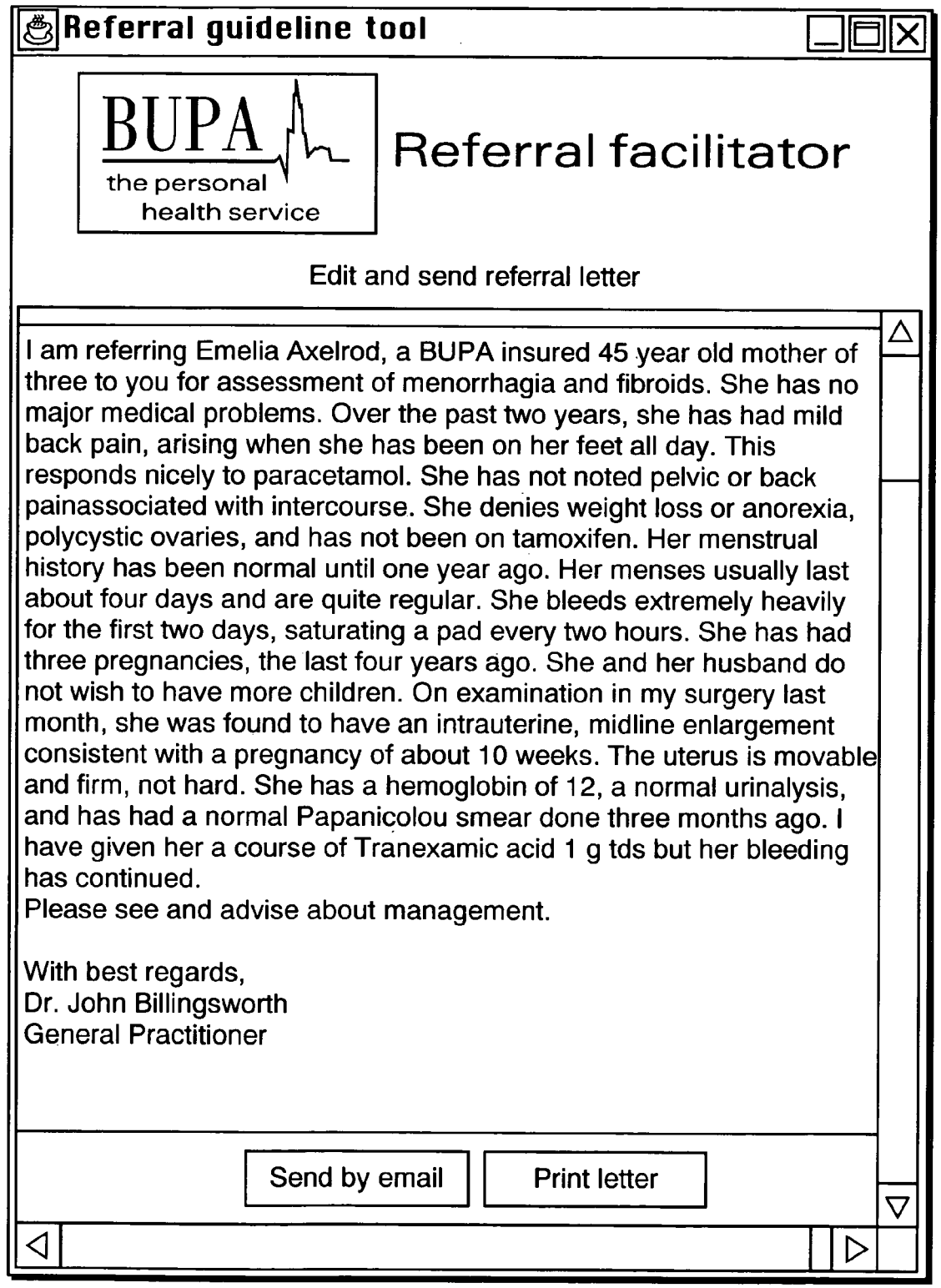
FIG. 9 depicts the computer generated referral note.

FIGS. 4-9 show screen shots of the primary care clinician screens. Screens are point and click, making them easy to use with personal digital assistants that can be used in the examination or consulting room. FIG. 4 depicts the personal identification of the referring primary care clinician, drawn from and updated into the insurer's database. FIGS. 5 and 6 show the checklist items for referral, using a gynecologic referral as an example. FIG. 7 shows the feedback screen, once the inference engine has determined if criteria have been met or not. FIG. 8 shows specialty-specific specialists, which can be automatically pulled from the insurer's database using a simple algorithm of location, for instance, or other desired criteria. The list of specialists can also include an indicia 29 which indicates whether or not the specialist also uses the system, or meets other desired performance criteria. FIG. 9 is an example of the patient's referral letter, which can be automatically and algorithmically generated from the information input by the primary care clinician and pulled from the insurer's data base.

In one aspect, specialists can also enter process suggestions into the system that can be automatically reported back to the primary care physician at the time of a referral. For instance, the specialist might indicate that he or she would like to have the patient prepared for their visit in a certain way, like showing up 15 minutes early, or filling out certain forms, etc., prior to the visit. In some embodiments, the specialist can modify the clinical decision pathway, and thus the checklist, to account for the unique preferences of the specialist, so long as the basic logic of the guideline was maintained. For example, a specialist might prefer an alternative type of test or workup where the medical literature did not support one alternative or the other. In this case, the algorithmically-generated checklist could be modified to some degree to account for these types of individual preferences, so long as they were reasonably consistent with the medical literature and the views of other experts in the field.

Figure 10:
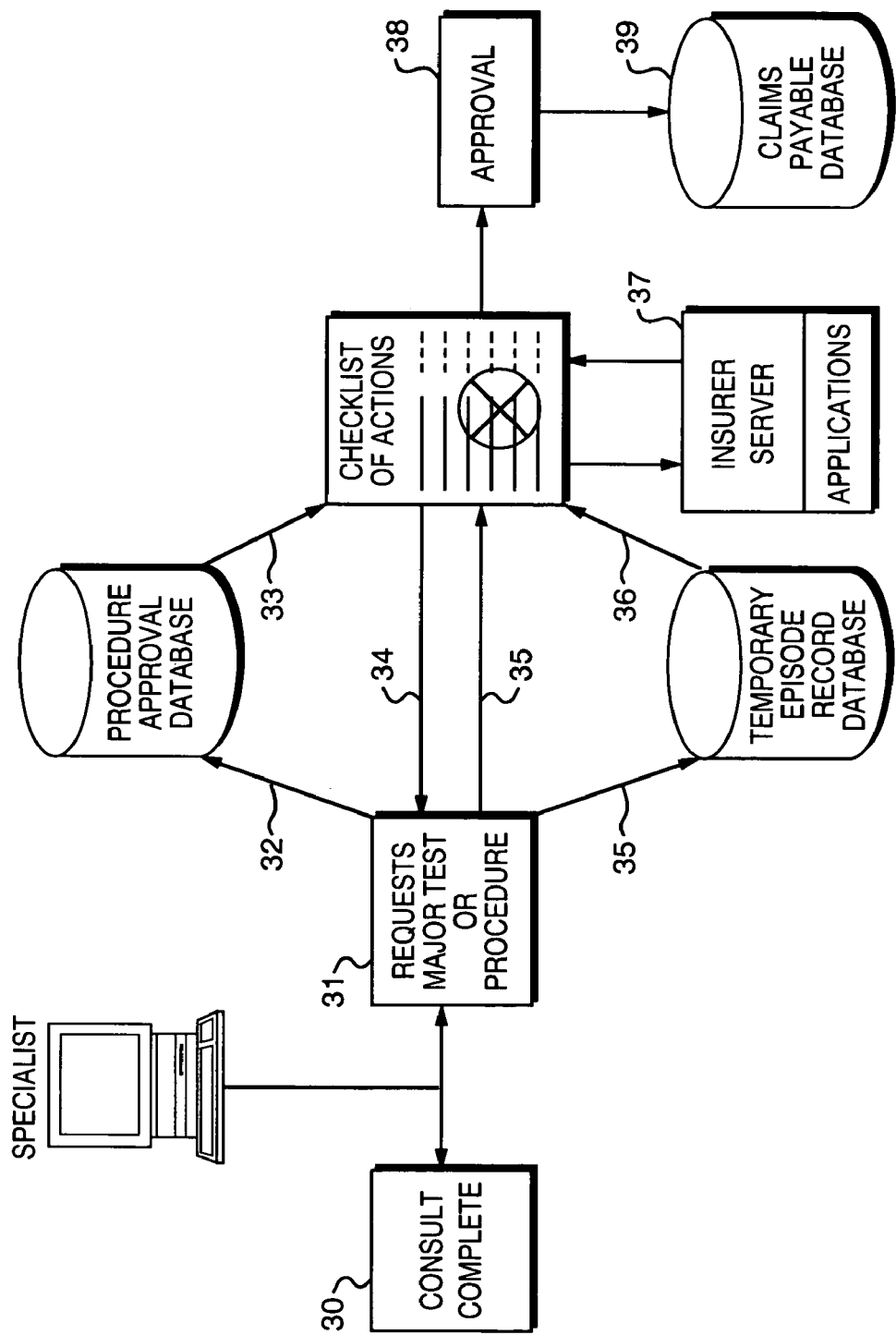
FIG. 10 is a low-level flow diagram of the specialist system.

FIG. 10 represents a low-level flow diagram of the specialist interaction with the system. After completing the consultation on the referred patient, the specialist logs on the system through an Internet connection from any of multiple user interfaces 102. Using a PIN number, the specialist enters the patient identification number, activating the temporary episode record 35. The specialist then may return the patient to the referring primary care clinician with a notification that the consult is complete 30 and/or a consultation note (which may be entered into the system as free text and/or prestructured options) or decide to request further tests or procedures 31. In the latter case, the specialist identifies the planned test or procedure 32 from a list, and the system utilizes prior patient data to generate a unique action checklist 33 from a procedure approval database. This unique list is presented to the specialist on the GUI as a checklist of actions 34, similar to the previously-described checklist that is presented to the referring physician for authorization for a referral. Prior data 36 residing in the database are automatically drawn from the temporary episode record of the patient to populate the checklist 34. Interacting with the checklist, the specialist enters remaining requested data 35. Data are checked against a decision algorithm operating in an insurer's or other entity's server 37. Once action criteria have been satisfied, approval 38 is posted to the specialist user interface, and can be automatically transmitted to the claims payable database 39.

Figure 11:
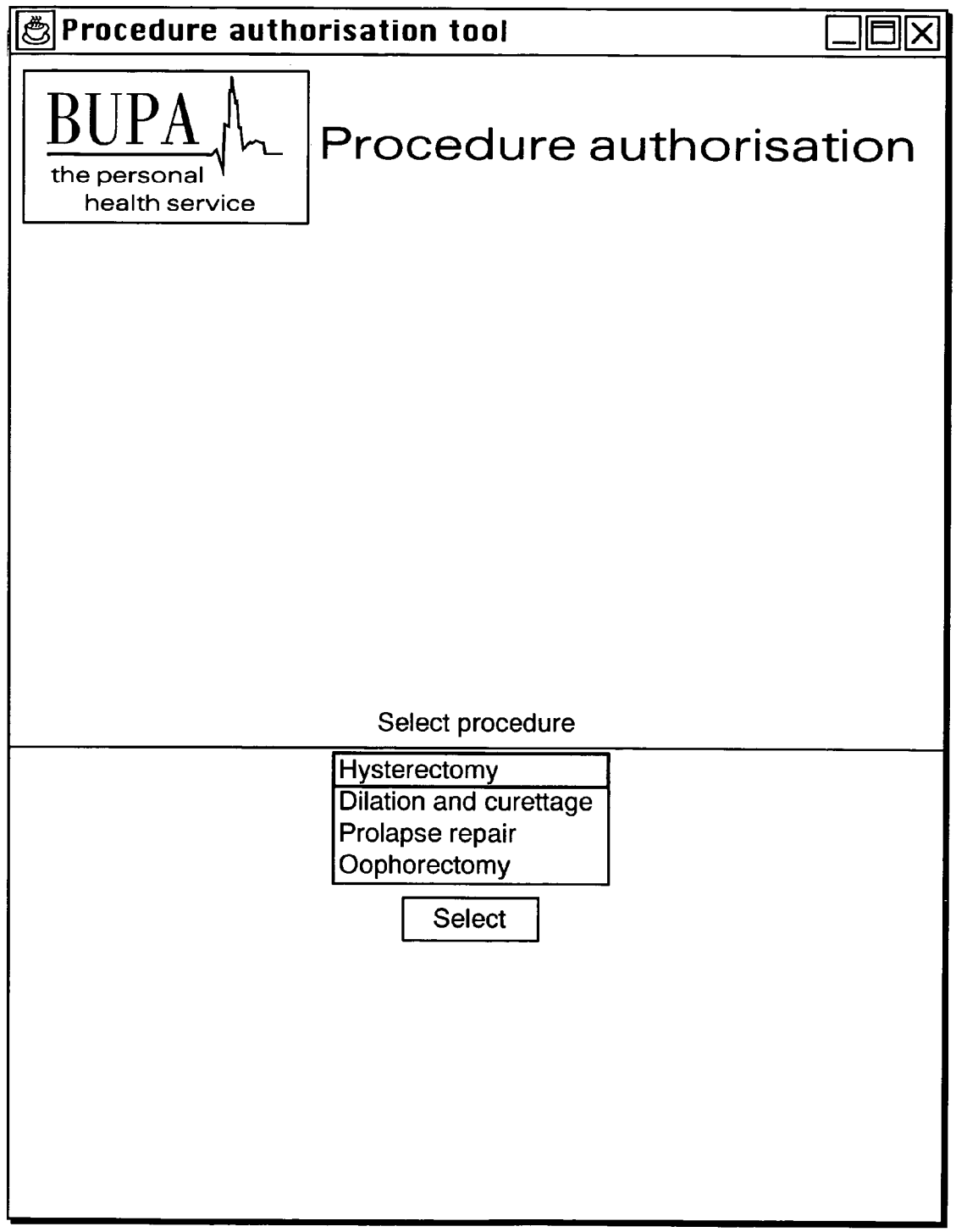
FIG. 11 depicts the specialist's screen for selecting a procedure.
Figure 12:
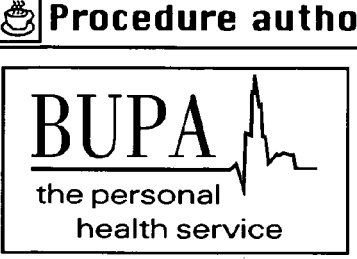
FIG. 12 displays the specialist's criterion referenced checklist gating approval of the procedure.
Figure 13:
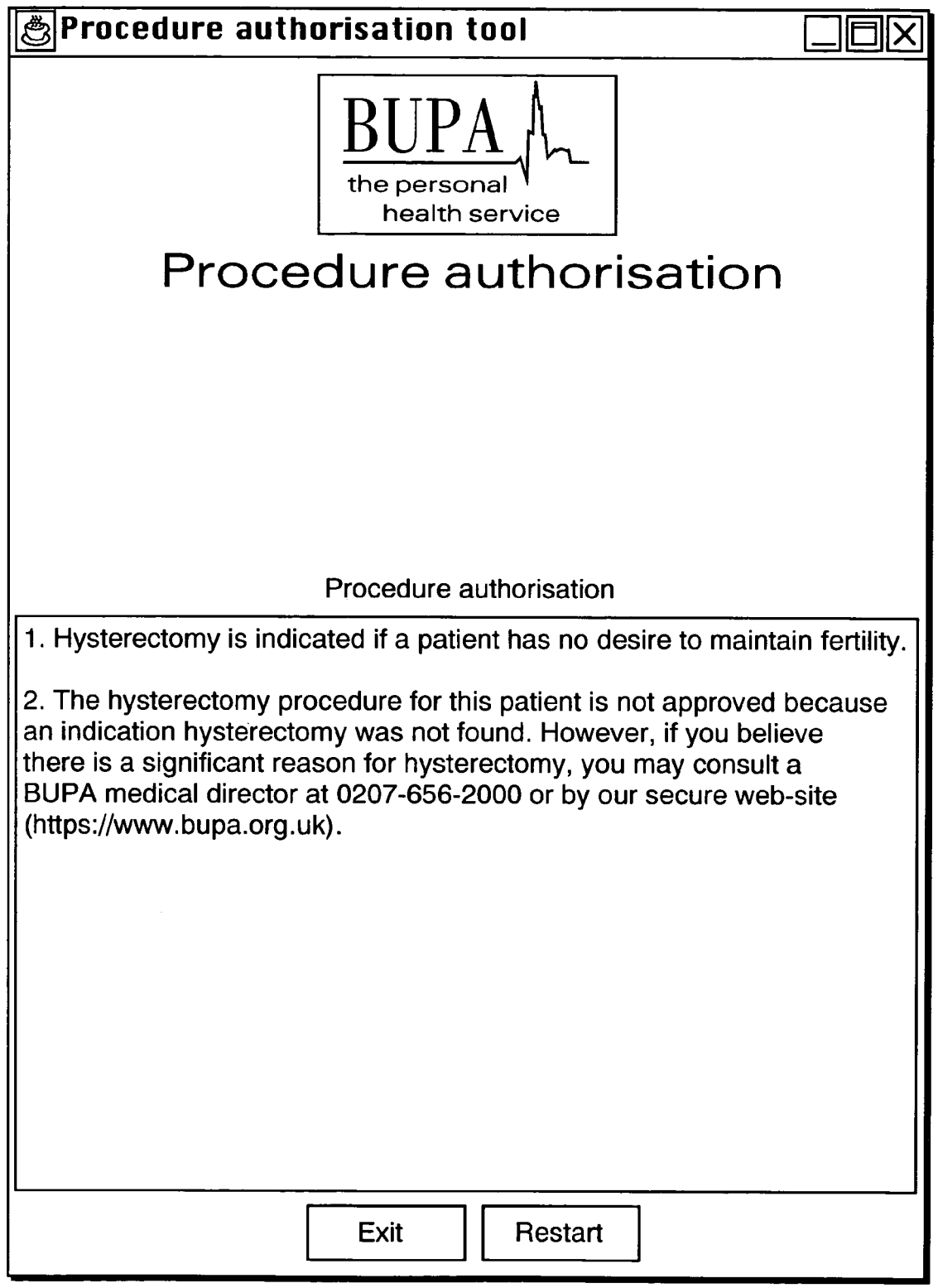
FIG. 13 displays the specialist's screen of approval or other actions needed.

FIGS. 11-13 are screen shots of specialist user interactions with the system. FIG. 11 shows a partial list of procedures that a gynecological specialist would choose from when requesting approval for a planned procedure. FIG. 12 shows an example of one point-and-click representation of the action step checklist of information required to assess whether criteria have been met. FIG. 13 demonstrates the feedback to the specialist regarding whether the procedure has met criteria for approval.

Figure 14:
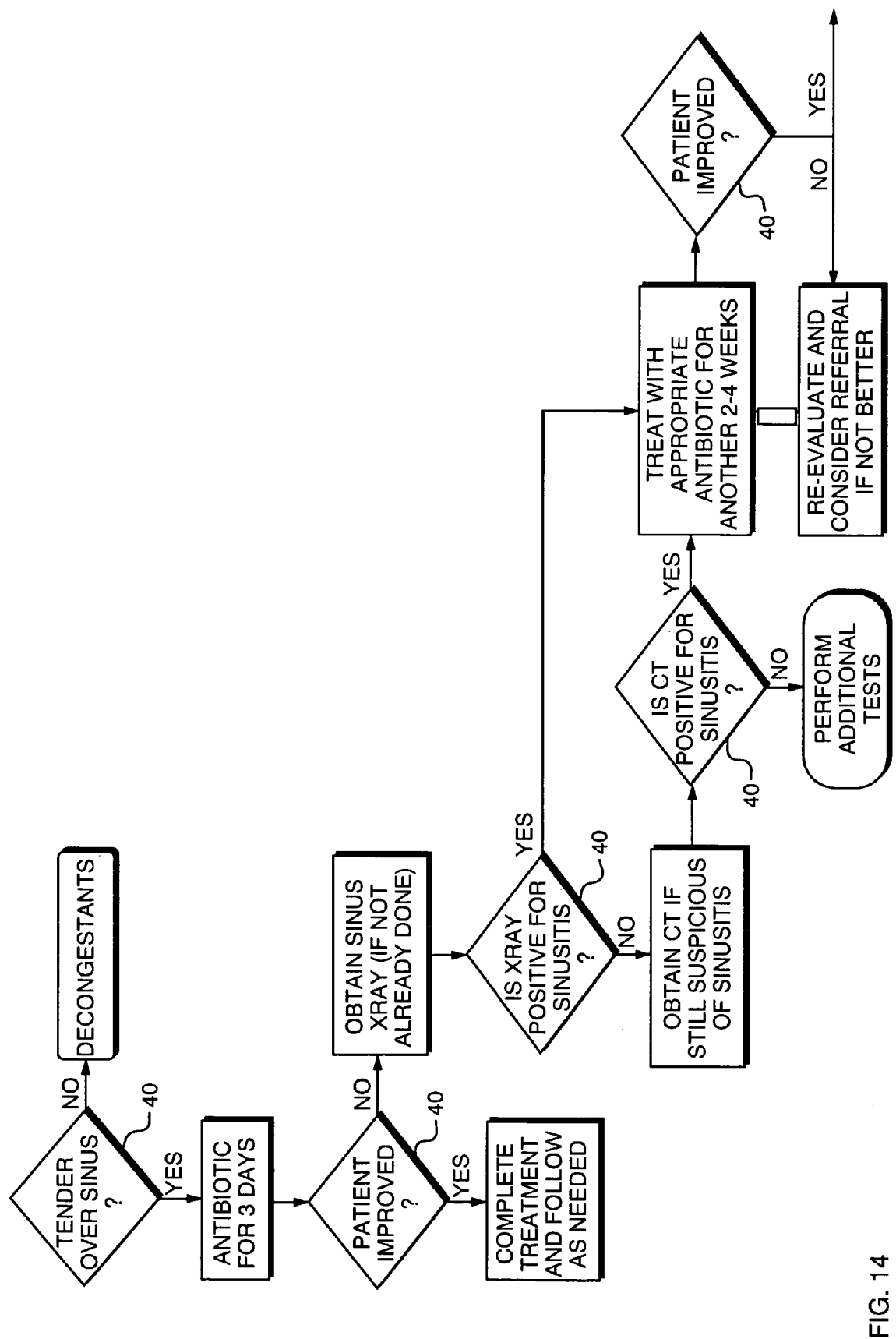
FIG. 14 displays a typical clinical guideline.

FIGS. 14-17 depict the method by which checklists are constructed from publicly available expert, evidence-based guidelines. FIG. 14 depicts a representative clinical guideline arranged as a branching decision tree. This example, for sinus infection, is typical of hundreds of such guidelines available on public web sites such as www.guideline.gov without charge. Guidelines are sequential steps in the work up and care of a designated clinical condition. Actions are followed by an outcome or decision step 40 consisting of a branching alternative that depends on the result of the action. Such guidelines have been developed and deployed for many years, but research shows that they are generally not used much by doctors.

Figure 15:
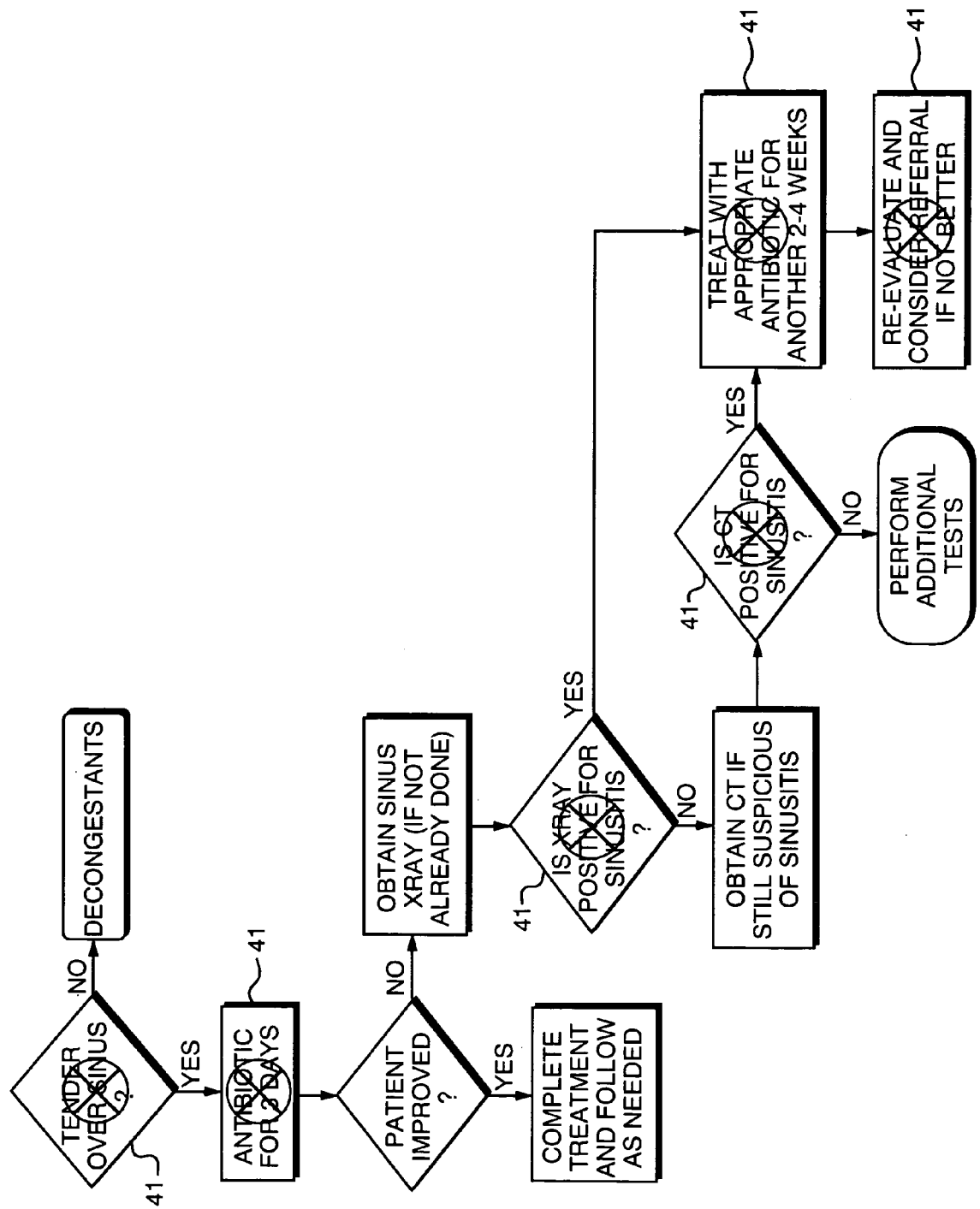
FIG. 15 displays the derivation and representation of critical, required action points.
Figure 16:
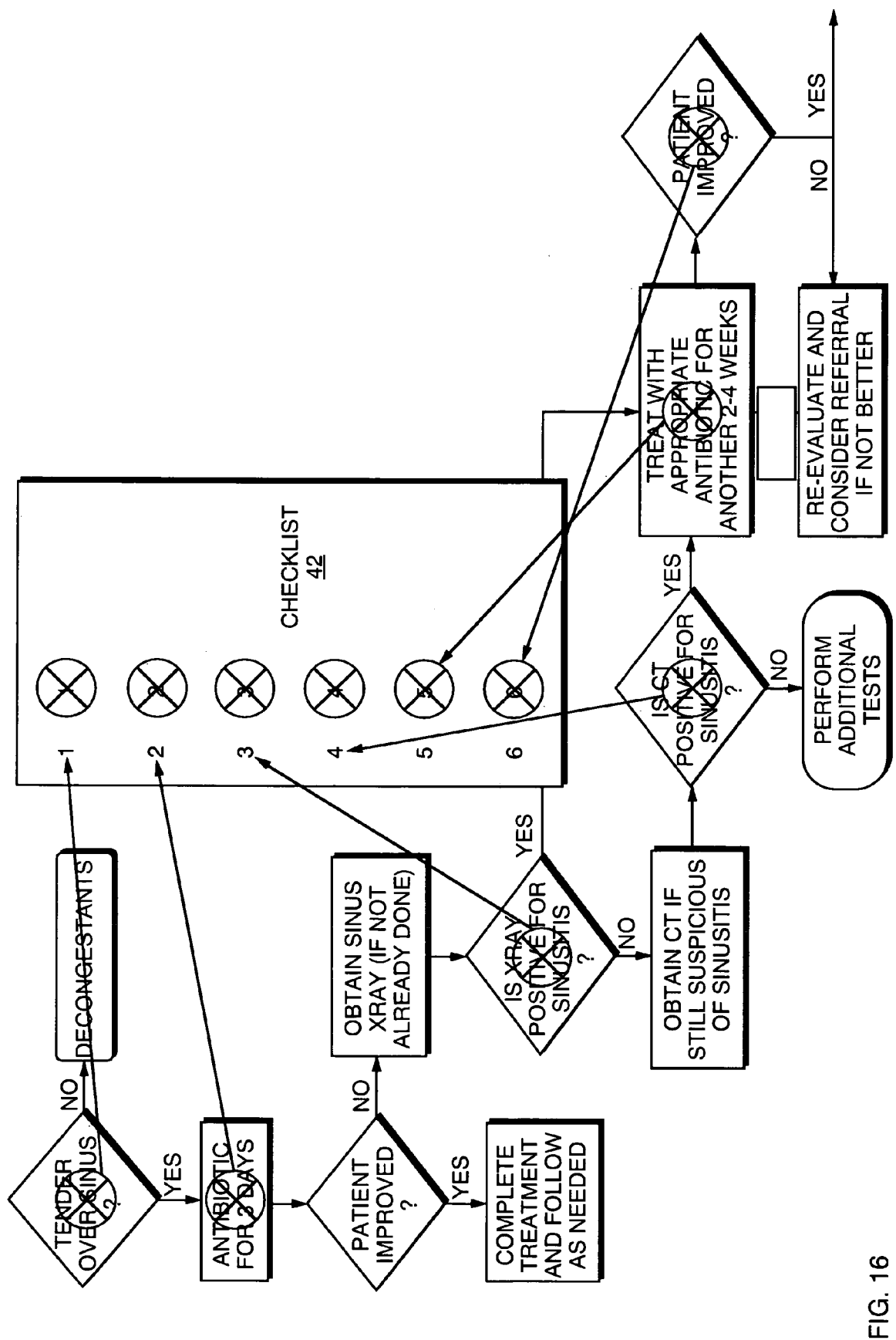
FIG. 16 is a schematic showing the creation of a checklist.

FIGS. 15 and 16 show the first step in transforming the guideline into a checklist. Action points, where an intervention (an item of medical history, a physical examination maneuver, or a test or procedure) of some type is performed and data collected, are identified 41. These data points mark the progressive movement of the clinical care along the decision tree. The figure displays these critical, required action points for the demonstration guideline. For this simple guideline, the action points could be displayed sequentially (FIG. 16) as a checklist of required items on a decision path 42. However, a checklist that merely builds off usual guidelines is not an adequate set of actions to represent optimal decision making. Optimal decision making is the minimum set of actions or steps needed to get to a pre-determined point of major transition in the process of care (to refer, to do further testing, to perform a surgical procedure, or to determine that the patient does not have the suspect condition). This set varies both by the probability or odds that a patient has the condition at each step of the decision tree and the optimal sequencing will vary depending on results from prior steps. The minimum, or optimal, path depends on data manipulations that includes knowledge of the prior probability of the condition for which the doctor is proposing any specific maneuver or action and the change in probability resulting from additional data inputs resulting from the specific action step. The basic formula used to calculate these "post-treatment probabilities" is called Bayes' Theorem.

Figure 17:
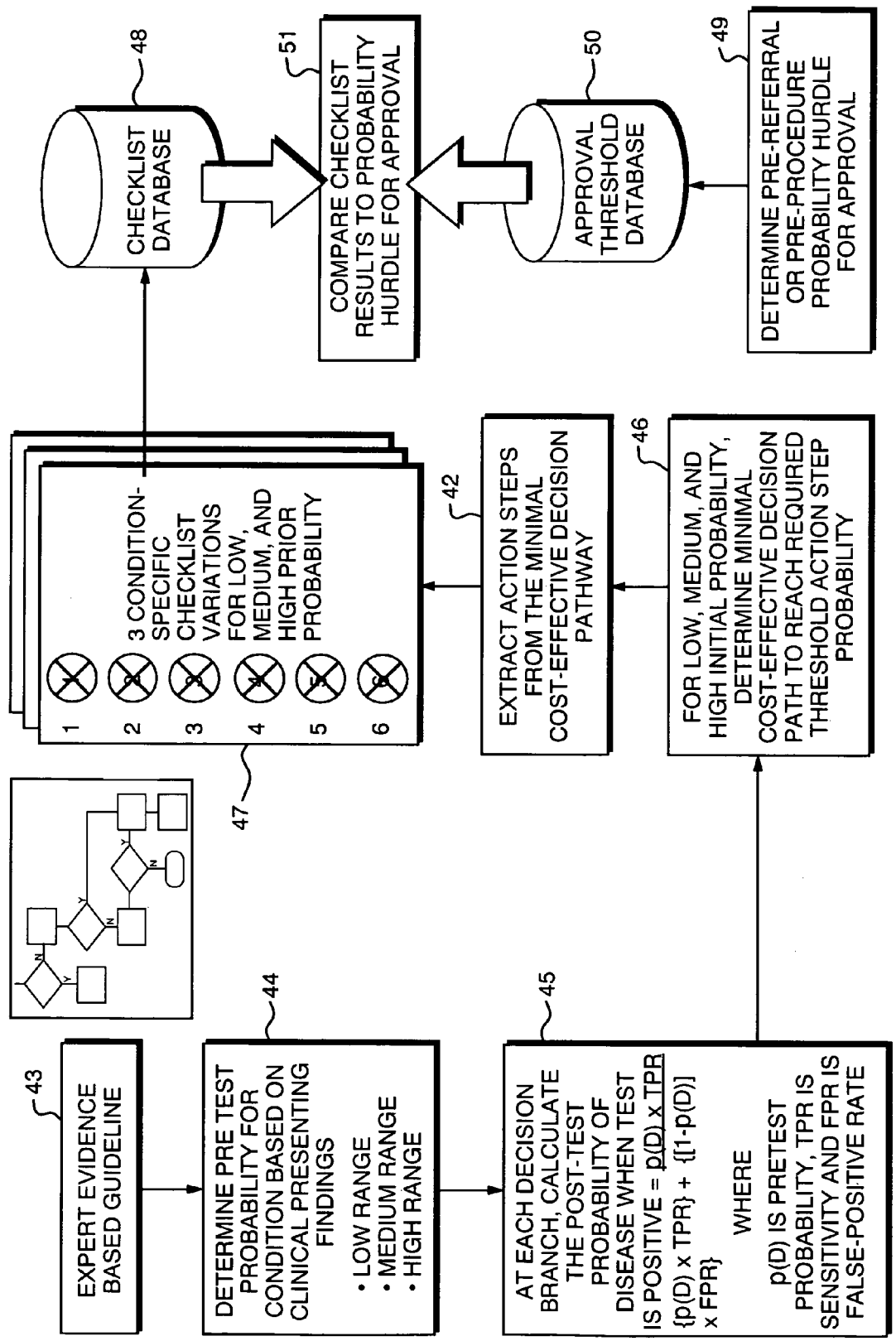
FIG. 17 is a flow diagram showing the process of using the Bayes' theorem formula to construct sets of preferred checklist sequences.

FIG. 17 shows how Bayes' theorem is used in creating an optimal checklist for the specific patient under care. For each and every condition, a decision tree is selected from public sources and modified by expert input 43. For each condition, a set of presenting symptoms and physical examination findings is defined. Based on combinations of these findings (present or absent) and a patient's personal history of risks of the condition and the frequency of the condition in the population that represents the group to which the patient belongs, an initial probability level of the condition is established. In the embodiment illustrated here, three levels of prior probability of the condition—low, medium, or high—are defined 44. Given the three states of prior probability, each step in the decision tree is subjected to Bayes' theorem calculation based on the pretest probability and the sensitivity and false-positive rate (i.e. specificity) of the condition 45. Based on each of the three starting probabilities, an optimal (least risk, least cost, best increased probability) sequence of steps can be constructed to reach an agreed level of probability of the condition 49. Each sequence will differ in its elements and sequencing based on the level of initial prior probability. Thus, three decision trees are created, and each is subject to an extracting process in which the action steps are identified 42 and published as a checklist. These checklists, for all conditions and for all defined prior probability states for the condition, are stored in a checklist database 48. For each of three "gates" or points of major transitions in care (decision to refer to a specialist, decision by a specialist to perform high risk/high cost tests, and decision to perform a procedural intervention) an analysis of the risks and benefits of the intervention is conducted, based on literature, and a prior probability approval threshold for the condition is identified at which the risks and the benefits of the procedure exactly balance 49, assuming the patient is neutral about these. These risks and benefits can also be modified by individual patients, using utility theory approaches, and could be used to raise or lower the probability threshold for the action to take place. These probability thresholds are defined as the level needed for approval of the step (opening the gate) and are stored in an approval threshold database 50. The system compares the cumulative probability from the checklist results to the threshold approval probability to determine if the threshold has been met 51.

Figure 18:
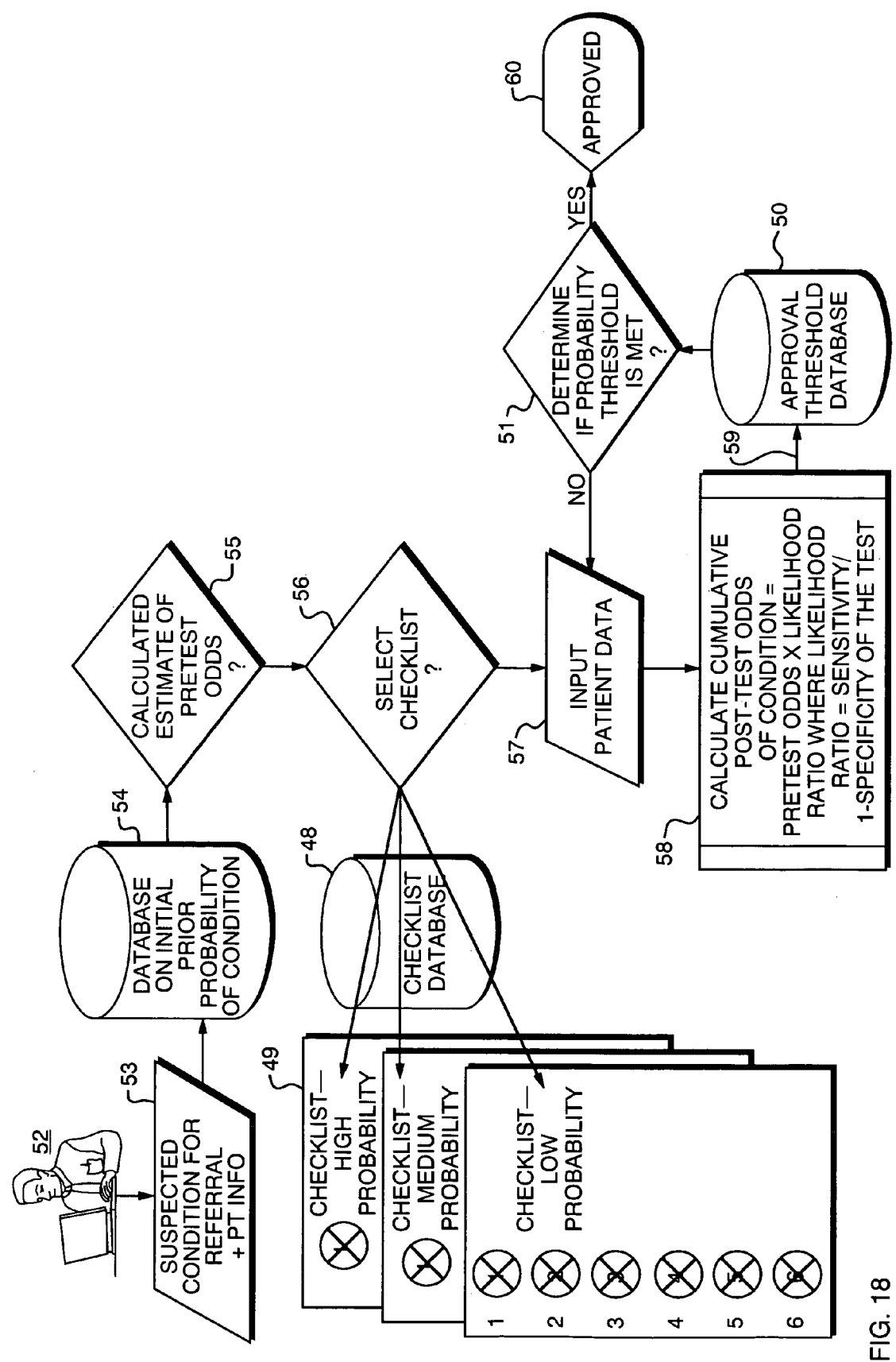
FIG. 18 is a flow diagram depicting the use of the primary care clinician's use of the checklist-based flow and tracking system.

FIG. 18 is a flow diagram depicting a primary care clinician's use of the checklist-based flow and tracking system. From any user interface, a primary care clinician accesses the system 52 via the Internet. Responding to questions based on the selected referral specialist, the clinician enters patient data that defines the suspected condition at the beginning of the work up 53. Drawing from a database 54 of initial probabilities, the system estimates the initial probability, or pre-test odds 55 of the condition. This calculation classifies the condition as low, medium or high probability and leads the system to draw 56 the appropriate checklist 49 from the checklist database 48. In one aspect, the prior probability of the patient's diagnosis can be estimated by a decision algorithm that assigns the patient to a prior probability level (e.g. low, medium, or high) based upon inputs such as patient data, medical history, information from the medical literature, and frequency of the condition, particularly within groups of people of whom the patient is a member. In a preferred embodiment, the prior probability algorithm estimates the patient's prior probability based on, at least in part, an analysis of the accumulated experience of many patients as represented in a system-wide database of all patients using the system. In this way, the accuracy of the prior probability estimates will be improved as more and more insurers, doctors, and patients utilize the system, thus creating a larger historical record of many different patient experiences and medical conditions.

Once the system produces 56 the appropriate checklist 49 from the checklist database 48, the clinician then enters responses to the checklist based on patient data 57. In general, if the patient's initial probability of having the condition is high, the checklist will be short; if low, the checklist will be longer, in order for the cumulative posterior probability (the probability as calculated following the incorporation of additional new data) to equal or exceed the approval threshold. As each checklist item is entered, the system calculates the posterior probability of the suspect condition according to algorithms 58 and compares 59 the result to the threshold probability in the approval threshold database 50 required for referral 51. As the cumulative post-test odds rise to or above the threshold, the system approves the referral 60. If the threshold is not met and checklist items are exhausted, the referral is not approved.

In certain embodiments, the threshold database 50 can also include criteria for rejecting a proposed medical action if the calculated probability of patient having the suspect medical condition falls below a predetermined minimum probability level. Preferably, this is in addition to the threshold approval criteria discussed above. For example, a checklist of data points for approval of a proposed medical action, such as a referral or a procedure, is generated based upon the estimated initial probability of a medical condition. As the requested data for each checklist item is entered by the user, the system calculates the posterior probability of the suspect condition according to probability theory. This posterior probability of the condition is then compared to both an approval threshold and a rejection threshold. If the posterior probability exceeds the approval threshold, then the proposed medical action satisfies the system's criteria, and an approval is returned. On the other hand, if the posterior probability drops below a certain minimum probability level, or rejection threshold, then the system will return a rejection of the proposed medical action. If the posterior probability is neither greater than the approval threshold, nor less than the rejection threshold, then the process is repeated for the next item on the checklist until all items are exhausted.

According to another aspect, as each successive data point is entered into the checklist, the inference engine can use the change in the patient's probability level to reassess the value of remaining data points on the clinical care pathway, and dynamically modify the number and sequence of subsequent data points on the checklist to account for these changed probabilities.

Figure 19:
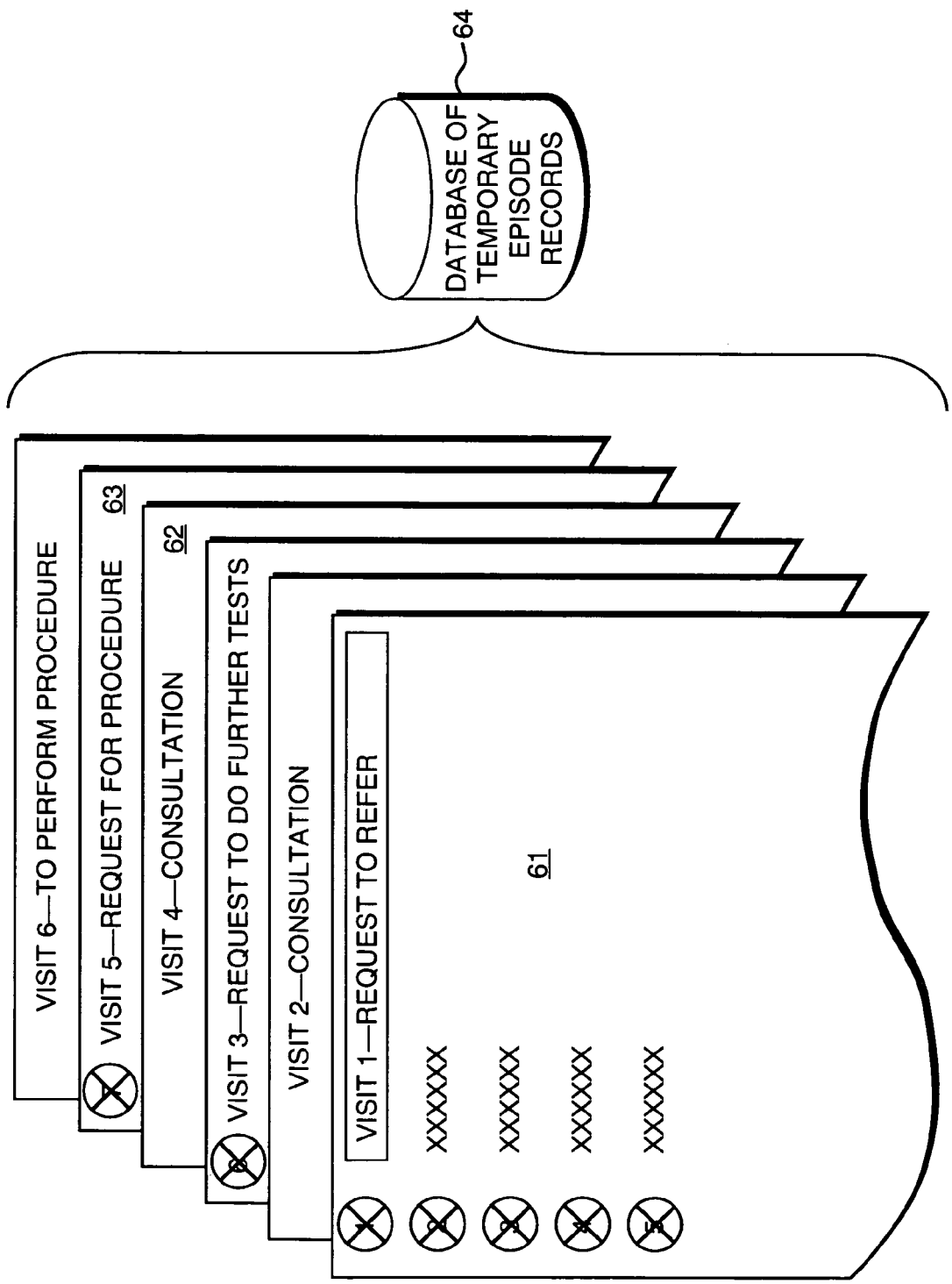
FIG. 19 displays the use of the checklist over multiple visits and assembly into a temporary episode record.

FIG. 19 is a schematic showing use of a checklist over multiple visits and assembly into a temporary episode record. A Bayesian-derived checklist is a unique representation of the best, and most minimal, (efficient and effective) decision guideline for the management of an episode of care for a given condition. As a clinician enters the process of care at specific transition points (referral to specialist, request for further tests, and request for approval for a procedure), the checklist is structured to act like a lock, and meeting the checklist criteria represents the key to open the gate at that point. Clinical actions take place as part of a series of patient visits, first with the primary care clinician and then with specialists after the patient has been referred. While the checklist is formally accessed at those visits corresponding to a transition point 61, 62, 63 the checklist represents an integrated series of steps on the optimal path of care, integrating actions throughout the process, like a kind of value chain, in which additional input moves the patient along a path towards resolution of the condition. Data could be entered at any encounter of the patient with the system of care, but only at the specified transition points are the answers to the checklist items treated like a key to open the gate to the requested action. Thus, the collection of checklist responses, as they are progressively entered, becomes a type of medical record of medical work up transactions, albeit in a truncated, skeletal form. This collection of checklist elements across all encounters and arranged in temporal sequence is stored as a temporary episode record in a secure database 64.

Figure 20:
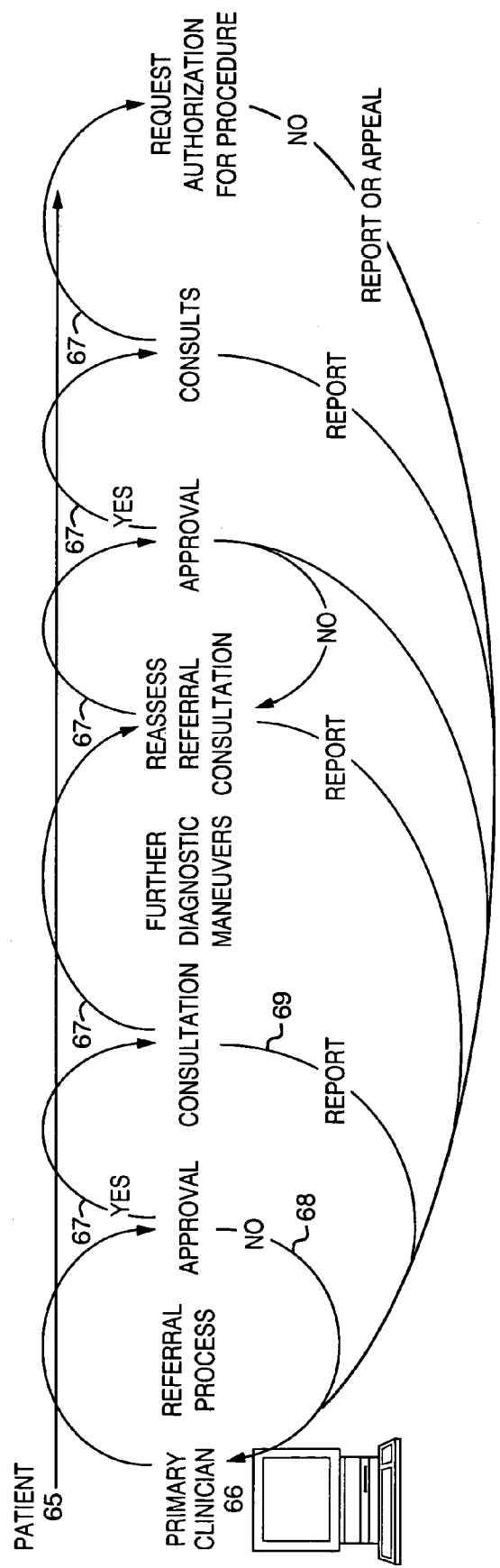
FIG. 20 depicts a flow diagram showing feedback loops to primary care clinician to provide data for monitoring and managing the supply chain.

FIG. 20 is a flow diagram showing feedback loops to a primary care clinician to provide data for that clinician to monitor and manage specialist care. As a patient's care evolves 65 over a clinical episode, a sequence of stages and transitions takes place 67. These stages represent progress along a sequence between referral and resolution of the problem episode, much like different staging points on the assembly line of an automobile. These stages are heralded by a transition in management, usually based upon reaching a point in a decision process where the probability threshold is reached that makes the transition appropriate. The work up consists of undertaking linked actions (examination, history, tests, and procedures) each of which contributes cumulatively to the probability of the condition. In this system, progress can be marked through the use of a checklist that is keyed to the proposed transition to the next stage. At this transition point, criteria justifying the transition may be met or not. The system tracks the patient's progress. At these transitions the system automatically publishes the approval decision 68—yes or no—to the referring primary care clinician, and provides the underlying checklist documentation if requested. The electronic episode record can also serve as the communication vehicle for publishing results of consultations and reports back to the referring primary care clinician. 69

Figure 21:
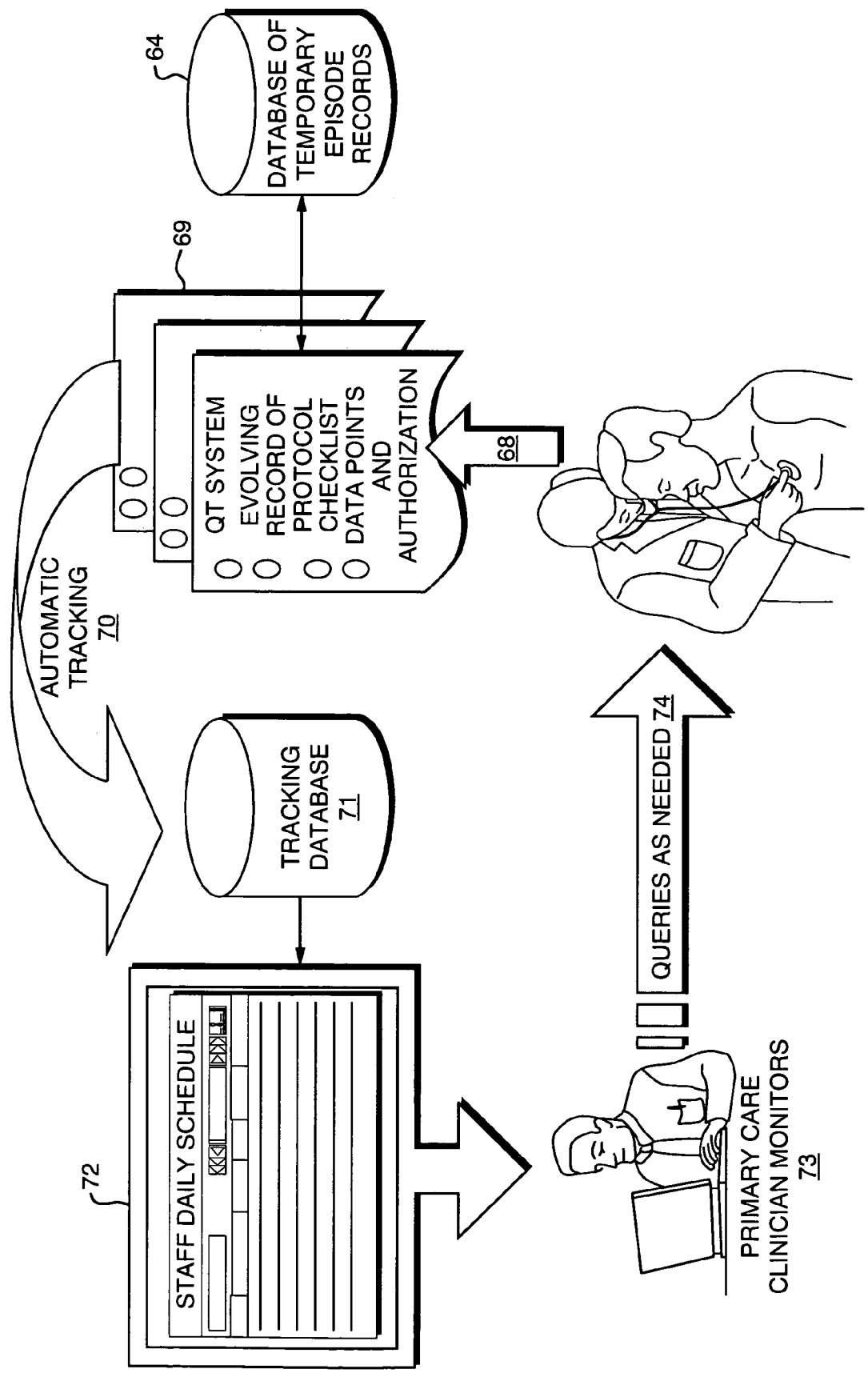
FIG. 21 is a high-level block flow diagram showing the feedback and monitoring mechanism.

FIG. 21 shows a high-level block flow diagram showing the feedback and monitoring mechanism for one embodiment of the system. Using any interface, a specialist 68 accesses the patient's temporary episode record from the database 64. The specialist responds interactively to the checklist 69, ordering and adding data either manually or automatically. At a transition to another stage, the system presents the specialist with a lock, which the checklist data either opens or not, authorizing the patient's movement to the next stage. These transactions are monitored and tracked automatically 70 and are posted to a tracking database 71. The tracking database can be accessed automatically at the time of login of the referring primary care clinician 73, who receives, via a user interface, a representation of the status of all his or her patients active in the specialist sector 72. Concerns, discrepancies, disputes, or problems can be communicated via the system 74 as asynchronous messages to the specialist and operated upon in text form by the specialist, as needed.

FIG. 22 depicts the primary care specialist tracking summary screen. This screen, on any GUI, encapsulates the status of all patients currently active in the specialist sector 76. Status of the patient is summarized using a color-coded (red, orange, green) designation 75 of the patient with serious discrepancies or problems through to one whose care and decisions are on track. Descriptive data such as length of time in specialist care 77 and discrepancies between checklist and actual data are highlighted. By double clicking on the colored status summary button 75, a detailed chart of visits and checklist items is displayed (FIG. 23).

While this invention has been particularly shown and described with references to preferred embodiments thereof, it will be understood by those skilled in the art that various changes in form and details may be made therein without departing from the scope of the invention encompassed by the appended claims.

What is claimed is:

1. A computer-implemented method of managing health care provided to a patient, comprising:

creating, by at least one computer, a plurality of checklists each associated with a prior probability level of a medical condition, wherein said creating includes transforming at least one stored evidence-based decision guideline into each of said plurality of checklists by using a Bayesian analysis to construct an optimal sequence of steps to reach a predetermined probability threshold indicating approval for a major transition in the care process;

storing, by said at least one computer, said plurality of checklists in a checklist database;

receiving, by said at least one computer, patient information entered by a first physician including a suspected medical condition and patient insurance information;

responsive to said patient information being received from said first physician, calculating, by said at least one computer, an initial prior probability of said suspected medical condition from said received patient information based on accumulated information from a plurality of other patients stored on an accessible system wide database;

selecting, by said at least one computer from said checklist database, a first checklist associated with a prior probability level of a medical condition matching said calculated initial prior probability of a suspected medical condition for said patient;

displaying, by said at least one computer, said first checklist to said first physician;

receiving, by said at least one computer, responses to said first checklist from said first physician;

calculating, by said at least one computer, a cumulative probability of said suspected medical condition based on said received responses to said first checklist from said first physician;

determining, by said at least one computer, that said cumulative probability of said suspected medical condition exceeds a predetermined probability threshold associated with said first checklist in said checklist database;

responsive to said predetermined probability threshold being met, determining, by said at least one computer, a first major transition in the care process including that said patient is to be referred to a second eligible physician with regard to said suspected medical condition based on said patient insurance information and physician identifying information from an insurance database;

responsive to said determining said first major transition in the care process, transmitting, by said at least one computer, a referral note to said second physician;

receiving, by said at least one computer, a proposed medical action selected by said second physician from a list of possible medical actions;

responsive to receiving said proposed medical action from said second physician, calculating, by said at least one computer, a subsequent prior probability of said suspected medical condition from said received patient information and said received proposed medical action based on accumulated information from a plurality of other patients stored on said accessible system wide database;

selecting, by said at least one computer from said checklist database, a second checklist associated with a prior probability level matching said calculated subsequent prior probability for said patient;

displaying, by said at least one computer, said second checklist to said second physician;

receiving, by said at least one computer, responses to said second checklist from said second physician;

calculating, by said at least one computer, a cumulative probability of said medical condition based on said received responses to said second checklist from said second physician;

determining, by said at least one computer, that said cumulative probability exceeds a predetermined probability threshold associated with said second checklist in said checklist database;

responsive to said predetermined threshold being met, determining, by said at least one computer, a second major transition in the care process including that said proposed medical action is to be performed on said patient with regard to said suspected medical condition;

responsive to said determining that said medical action is to be performed on said patient, generating, by said at least one computer, an approval of said proposed medical action; and responsive to said generating of said approval of said proposed medical action, automatically reporting to said first physician, by said at least one computer, said approval of said proposed medical action together with said responses to said second checklist received from said second physician.

2. The method of claim 1, further comprising:

storing, by said at least one computer system, said patient information received from said first physician, said suspected medical condition, said calculated initial prior probability for said patient with regard to said first major transition in the care process, said first checklist, said responses to said first checklist received from said first physician, said referral note, said proposed medical action selected by said second physician, said second checklist, said responses to said second checklist received from said second physician, and said approval of said proposed medical action, into a temporary episode record contained in a temporary episode record database.

3. The method of claim 2, further comprising:

storing, by said at least one computer system, said temporary episode record in said system wide database.

4. The method of claim 3, further comprising:

purging, by said at least one computer system, said temporary episode record of patient identification information prior to storing said temporary episode record in said system wide database.

5. The method of claim 1, further comprising:

wherein said reporting said approval of said proposed medical action to said first physician comprises displaying a progress report in a graphical user interface, wherein said progress report summarizes the status of all of the first physician's patients currently undergoing active care by specialists.

6. The method of claim 5, further comprising:

wherein said progress report that summarizes the status of all of the first physician's patients displays color codes representing the status of each of said patients currently undergoing active care by specialists.

7. The method of claim 1, further comprising:
wherein said information stored in said system wide database regarding said plurality of other patients comprises data from temporary episode records of said plurality of other patients.

8. The method of claim 7, further comprising:
wherein said calculating of said calculated prior probability for said patient with regard to said first major transition in the care process and said calculating of said calculated prior probability for said patient with regard to said second major transition in the care process are responsive to said data from said temporary episode records of said plurality of other patients.

9. The method of claim 1, further comprising:
wherein said initial prior probability level comprises one of the set consisting of high probability, medium probability, and low probability.

10. The method of claim 1, further comprising:
wherein said first physician comprises a primary care physician; and
wherein said second physician comprises a specialist.

11. The method of claim 1, further comprising:
wherein said proposed medical action comprises a test.

12. The method of claim 1, further comprising:
wherein said proposed medical action comprises a medical procedure.

13. The method of claim 1, further comprising:
wherein said proposed medical action comprises a medical treatment.

14. The method of claim 1, further comprising:
determining, by said at least one computer system, that said responses to said first checklist received from said first physician do not satisfy evidence-based clinical decision criteria for referring said patient to said second physician; and
responsive to said determination that said responses to said first checklist received from said first physician do not satisfy said evidence-based clinical decision criteria for referring said patient to said second physician, generating, by said at least one computer system, a notification to said first physician.

15. The method of claim 1, further comprising:
determining, by said at least one computer system, that said responses to said second checklist received from said second physician do not satisfy evidence-based clinical decision criteria for approval of said proposed medical action; and
responsive to said determination that said responses to said second checklist received from said second physician do not satisfy said evidence-based clinical decision criteria for approval of said proposed medical action, generating, by said at least one computer system, a notification to both said first physician and said second physician.

16. A system for managing health care provided to a patient, said system including at least one computer and at least one database, comprising:
a decision engine in at least one computer system configured to create a plurality of checklists each associated with a prior probability level of a medical condition, wherein said creation includes transforming at least one stored evidence-based decision guideline into each of said plurality of checklists by using a Bayesian analysis to construct an optimal sequence of steps to reach a predetermined probability threshold indicating approval for a major transition in the care process;
a checklist database configured to store said plurality of checklists;
an accessible system wide database configured to store information regarding a plurality of other patients;
an insurance database configured to store physician identifying information;
said computer system, via a first user interface, configured to receive patient information entered by a first physician including a suspected medical condition and patient insurance information;
said computer system, responsive to said patient information being received from said first physician, configured to calculate an initial prior probability of said suspected medical condition from said received patient information based on accumulated information from a plurality of other patients stored on an accessible system wide database;
said computer system configured to select from said checklist database, a first checklist associated with a prior probability level of a medical condition matching said calculated initial prior probability of a suspected medical condition for said patient;
said computer system, via said first user interface, configured to display said first checklist to said first physician;
said computer system, via said user interface, configured to receive responses to said first checklist from said first physician;
said computer system configured to calculate a cumulative probability of said suspected medical condition based on said received responses to said first checklist from said first physician;
said computer system configured to determine that said cumulative probability of said suspected medical condition exceeds a predetermined probability threshold associated with said first checklist in said checklist database;
said computer system, responsive to said predetermined probability threshold being met, configured to determine first major transition in the care process including that said patient is to be referred to a second eligible physician with regard to said suspected medical condition based on said patient insurance information and physician identifying information from an insurance database;
said computer system, responsive to said determining said first major transition in the care process, configured to transmit a referral note to said second physician;
said computer system, via a second user interface, configured to display to said second physician said referral note to a second physician and a list of possible medical actions;
said computer system, via said second user interface, configured to receive a proposed medical action selected by said second physician from said displayed list of possible medical actions;
said computer system, responsive to receiving said proposed medical action from said second physician, configured to calculate a subsequent prior probability of said suspected medical condition from said received patient information and said received proposed medical action based on accumulated information from a plurality of other patients stored on said accessible system wide database;
said computer system configured to select from said checklist database, a second checklist associated with a prior probability level matching said calculated subsequent prior probability for said patient;

said computer system, via said second user interface, configured to display said second checklist to said second physician;

said computer system, via said second user interface, configured to receive responses to said second checklist from said second physician;

said computer system configured to calculate a cumulative probability of said medical condition based on said received responses to said second checklist from said second physician;

said computer system configured to determine that said cumulative probability exceeds a predetermined probability threshold associated with said second checklist in said checklist database;

said computer system, responsive to said predetermined threshold being met, configured to determine a second major transition in the care process including that said proposed medical action is to be performed on said patient with regard to said suspected medical condition;

said computer system, responsive to said determining that said medical action is to be performed on said patient, configured to generate, by said at least one computer, an approval of said proposed medical action; and said computer system, responsive to said generating of said approval of said proposed medical action, configured to automatically report to said first physician, via said at first user interface, said approval of said proposed medical action together with said responses to said second checklist received from said second physician.

17. The system of claim 16, further comprising:
a temporary episode record in a temporary episode record database configured to store said patient information received from said first physician, said suspected medical condition, said calculated initial prior probability for said patient with regard to said first major transition in the care process, said first checklist, said responses to said first checklist received from said first physician, said referral note, said proposed medical action selected by said second physician, said second checklist, said responses to said second checklist received from said second physician, and said approval of said proposed medical action.

18. The system of claim 17, further comprising:
a system wide database configured to store said temporary episode record.

19. The system of claim 18, further comprising:
wherein temporary episode record is purged of patient identification information prior to said temporary episode record being stored in said system wide database.

20. The system of claim 16, further comprising:
wherein said information stored in said system wide database regarding said plurality of other patients comprises data from temporary episode records of said plurality of other patients.

21. The system of claim 20, further comprising:
wherein said calculating of said calculated prior probability for said patient with regard to said first major transition in the care process and said calculating of said calculated prior probability for said patient with regard to said second major transition in the care process are responsive to said data from said temporary episode records of said plurality of other patients.

22. The system of claim 16, further comprising:
wherein said initial prior probability level comprises one of the set consisting of high probability, medium probability, and low probability.

23. The system of claim 16, further comprising:
wherein said first physician comprises a primary care physician; and
wherein said second physician comprises a specialist.

24. The system of claim 16, further comprising:
wherein said proposed medical action comprises a test.

25. The system of claim 16, further comprising:
wherein said proposed medical action comprises a medical procedure.

26. The system of claim 16, further comprising:
wherein said proposed medical action comprises a medical treatment.

27. The system of claim 16, further comprising:
wherein said at least one computer system is further configured to determine that said responses to said first checklist received from said first physician do not satisfy evidence-based clinical decision criteria for referring said patient to said second physician; and
responsive to said determination that said responses to said first checklist received from said first physician do not satisfy said evidence-based clinical decision criteria for referring said patient to said second physician, generate a notification to said first physician.

28. The system of claim 16, further comprising:
wherein said at least one computer system is further configured to determine that said responses to said second checklist received from said second physician do not satisfy evidence-based clinical decision criteria for approval of said proposed medical action; and
responsive to said determination that said responses to said second checklist received from said second physician do not satisfy said evidence-based clinical decision criteria for approval of said proposed medical action, generate a notification to both said first physician and said second physician.

29. The system of claim 16, further comprising:
wherein said reporting said approval of said proposed medical action to said first physician comprises displaying a progress report in a graphical user interface, wherein said progress report summarizes the status of all of the first physician's patients currently undergoing active care by specialists.

30. The system of claim 16, further comprising:
wherein said progress report that summarizes the status of all of the first physician's patients displays color codes representing the status of each of said patients currently undergoing active care by specialists.

* * * * *